United States Patent
Lee

(10) Patent No.: US 10,801,056 B2
(45) Date of Patent: Oct. 13, 2020

(54) KIT AND METHOD FOR DETECTION OF MICRORNA

(71) Applicant: HEIMBIOTEK INC., Hwaseong-si, Gyeonggi-do (KR)

(72) Inventor: Jae Hoon Lee, Guri-si (KR)

(73) Assignee: HEIMBIOTEK INC., Hwaseong-si (KR)

( * ) Notice: Subject to any disclaimer, the term of this patent is extended or adjusted under 35 U.S.C. 154(b) by 120 days.

(21) Appl. No.: 15/671,374

(22) Filed: Aug. 8, 2017

(65) Prior Publication Data

US 2017/0335375 A1    Nov. 23, 2017

Related U.S. Application Data

(63) Continuation-in-part of application No. PCT/KR2016/001411, filed on Feb. 11, 2016.

(30) Foreign Application Priority Data

Feb. 9, 2015  (KR) .................. 10-2015-0019784

(51) Int. Cl.
| | |
|---|---|
| *C12Q 1/6809* | (2018.01) |
| *C12Q 1/6853* | (2018.01) |
| *C12Q 1/6811* | (2018.01) |
| *C12Q 1/6816* | (2018.01) |
| *C12Q 1/6844* | (2018.01) |
| *C07H 21/04* | (2006.01) |
| *C12P 19/34* | (2006.01) |
| *C12Q 1/00* | (2006.01) |

(52) U.S. Cl.
CPC .......... *C12Q 1/6809* (2013.01); *C07H 21/04* (2013.01); *C12P 19/34* (2013.01); *C12Q 1/6811* (2013.01); *C12Q 1/6816* (2013.01); *C12Q 1/6844* (2013.01); *C12Q 1/6853* (2013.01); *C12Q 1/00* (2013.01); *C12Q 2525/207* (2013.01)

(58) Field of Classification Search
None
See application file for complete search history.

(56) References Cited

U.S. PATENT DOCUMENTS

| | | | |
|---|---|---|---|
| 8,192,937 B2 | 6/2012 | Jacobsen et al. | |
| 8,383,344 B2 | 2/2013 | Jacobsen et al. | |
| 2013/0045885 A1 | 2/2013 | Mohapatra et al. | |
| 2014/0227689 A1 | 8/2014 | Jacobsen et al. | |
| 2014/0295434 A1* | 10/2014 | Wu ........................ | C12Q 1/686 |
| | | | 435/6.12 |

FOREIGN PATENT DOCUMENTS

| | | |
|---|---|---|
| EP | 2198059 A1 | 6/2010 |
| KR | 20090017670 A | 2/2009 |
| WO | 2007143097 A1 | 12/2007 |

OTHER PUBLICATIONS

International Search Report dated Jun. 22, 2016 for PCT/KR2016/001411.

* cited by examiner

*Primary Examiner* — Young J Kim
(74) *Attorney, Agent, or Firm* — Lucas & Mercanti, LLP

(57) ABSTRACT

The present invention relates to a kit for detecting miRNA and a method for detecting miRNA using the kit. According to the miRNA detection kit and method of the present invention, it is possible to detect a certain miRNA in a quick and accurate manner, and it also possible to perform multiplex analysis capable of detecting a plurality of miRNAs at the same time.

3 Claims, 26 Drawing Sheets
Specification includes a Sequence Listing.

| Sample | | Cq | Melt Tem. |
|---|---|---|---|
| miR-362 | Unkn | 22.21 | 78.5 |
| miR-362 | Unkn | 22.35 | 78.5 |
| miR-362 | NTC | N/A | None |

| Sample | | Cq | Melt Tem. |
|---|---|---|---|
| miR-29c | Unkn | 17.49 | 78 |
| miR-29c | Unkn | 17.8 | 78 |
| miR-29c | NTC | N/A | None |

| Sample | | Cq | Melt Tem. |
|---|---|---|---|
| miR-127 | Unkn | 15.39 | 79 |
| miR-127 | Unkn | 15.13 | 79 |
| miR-127 | NTC | 35.03 | 89 |

KIT AND METHOD FOR DETECTION OF MICRORNA

CROSS-REFERENCE TO RELATED APPLICATIONS

This application is a continuation-in-part of PCT/KR2016/001411, filed Feb. 11, 2016, which claims the priority from Korean Patent Application No. 10-2015-0019784, filed Feb. 9, 2015, the contents of each of which are incorporated herein by reference.

TECHNICAL FIELD

The present invention relates to a kit and a method for detecting nucleic acid, and more particularly to a kit and a method for detecting microRNA.

BACKGROUND ART

MicroRNA (hereinafter abbreviated as "miRNA") is a noncoding RNA consisting of about 22 ribonucleotides. It is known that miRNA regulates gene expression in the post-transcriptional stage by silencing messenger RNA. This function of miRNA is performed by base-pairing with a complementary sequence in its targeted mRNA (Bartel, D. P., Cell, 136(2): 215-233, 2009).

Since miRNA was first found in *C. elegans*, a variety of miRNAs have been reported one after another while it is known that they can regulate gene expression in animals, plants and viruses. In addition, it is known that dysfunctions attributable to mutation of miRNA genes may cause certain diseases such as cancer (Mraz, M. and Pospisilova, S., Expert Rev. Hematol., 5(6): 579-581, 2012; Hughes et al., Am. J. Hum. Genet., 89: 628-633, 2011; Pontual et al., Nat. Genet., 43(10): 1026-1030, 2011; Lu et al., Nature 435(9): 834-838, 2005). Thus, the importance of miRNAs has been more and more recognized.

Since it is known that miRNA is very short in length (about 22 nt), there is great difficulty in isolating or detecting miRNA. Conventional methods for detecting miRNA include Northern blot analysis; detection-based hybridization using microarrays; a method of detecting and quantifying a certain miRNA by a two-step process comprising RT-PCR, which uses stem-loop primers binding complementarily to the miRNA, and subsequent quantitative PCR (Chen et al., Nucleic Acids Res., 33(20): e179, 2005); and a method comprising tailing the 3'-end of miRNA with poly(A) using a poly(A) polymerase, synthesizing cDNA using a poly(T) adaptor as a primer, and then amplifying the miRNA using a miRNA-specific forward primer and a reverse primer based on the poly(T) adaptor (Shi, R. and Chiang, V. L., BioTechniques, 39: 519-525, 2005).

However, the above-described detection methods have disadvantages in that, because complementary sequences are not enough long, nonspecific amplification can be occurred, and because these methods are generally based on real-time PCR, expensive real-time PCR systems are required, and because PCR products have similar sizes, multiplex analysis for detecting various miRNAs at the same time is limited.

SUMMARY OF INVENTION

The present invention has been made in order to solve various problems, including the above-described problems, and it is an object of the present invention to provide an easier and more economic kit and method for detecting miRNA. It is to be understood, however, this object is only illustrative and the scope of the present invention is not limited by the aforementioned object.

In accordance with one aspect of the present invention, there is provided a kit for detecting miRNA, comprising:

a short reverse transcription primer being more diffusible, consequently enhancing the efficacy of reverse transcription compared to previous ones, being composed of a first hybridizing oligonucleotide and a first adaptor oligonucleotide, the first hybridizing oligonucleotide having a nucleic acid sequence which hybridizes specifically to the 3'-end of a miRNA or the 3'-end of a poly(A)-tailed miRNA obtained by tailing a miRNA with poly(A) using a poly(A) polymerase, and the first adaptor oligonucleotide being attached to the 5'-end of the first hybridizing oligonucleotide and having any nucleic acid sequence which does not hybridize to the miRNA;

an extension primer longer than the reverse transcription primer and composed of a second hybridizing oligonucleotide and a second adaptor oligonucleotide, the second hybridizing oligonucleotide being capable of hybridizing specifically to a portion of a single-stranded cDNA reverse-transcribed from the miRNA or the poly(A)-tailed miRNA, the portion of the single-stranded cDNA excluding a portion corresponding to the 3'-end of the miRNA or the poly(A)-tailed miRNA, the 3'-end of the miRNA or the poly(A)-tailed miRNA being hybridized to the first hybridizing oligonucleotide, and the second adaptor oligonucleotide being attached to the 5'-end of the second hybridizing oligonucleotide and having any nucleic acid sequence which does not hybridize to the single-stranded cDNA; and a forward primer having a sequence within the sequence of the second adaptor oligonucleotide.

In accordance with another aspect of the present invention, there is provided a method for detecting miRNA, comprising:

reverse-transcribing a miRNA using a reverse transcriptase and a short reverse transcription primer that is more diffusible enhancing reverse transcription reaction due to the short length than that of the other miRNA assay product, and the short reverse transcription primer is composed of a first hybridizing oligonucleotide and a first adaptor oligonucleotide, the first hybridizing oligonucleotide having a nucleic acid sequence which hybridizes specifically to the 3'-end of the miRNA, and the first adaptor oligonucleotide being attached to the 5'-end of the first hybridizing oligonucleotide and having any nucleic acid sequence which does not hybridize to the miRNA;

deactivating the reverse transcriptase and melting a DNA produced by the reverse transcription, thereby preparing a single-stranded cDNA reverse-transcribed from the miRNA;

extending the single-stranded cDNA using a DNA polymerase and an extension primer longer than the reverse transcription primer, in which the extension primer is composed of a second hybridizing oligonucleotide and a second adaptor oligonucleotide, the second hybridizing oligonucleotide being capable of hybridizing specifically to a portion of the single-stranded cDNA reverse-transcribed from the miRNA, the portion of the single-stranded cDNA excluding a portion corresponding to the 3'-end of the miRNA, the 3'-end of the miRNA being hybridized to the first hybridizing oligonucleotide, and the second adaptor oligonucleotide being attached to the 5'-end of the second hybridizing oligonucleotide and having any nucleic acid sequence which does not hybridize to the single-stranded cDNA; and performing PCR amplification using as a template a double-strand cDNA produced by the extending and using a reverse primer having the same nucleic acid sequence as that of the reverse transcription primer or the first adaptor oligonucleotide, and a forward primer having a sequence within the sequence of the second adaptor oligonucleotide.

In accordance with still another aspect of the present invention, there is provided a method for detecting miRNA, comprising:

tailing a miRNA with poly(A) using a poly(A) polymerase, thereby preparing a poly(A)-tailed miRNA;

reverse-transcribing the poly(A)-tailed miRNA using a reverse transcriptase and a short reverse transcription primer, in which the short reverse transcription primer is composed of a first hybridizing oligonucleotide and a first adaptor oligonucleotide, the first hybridizing oligonucleotide being composed of poly dT which hybridizes specifically to the poly(A) tail of the poly(A)-tailed miRNA, and the first adaptor oligonucleotide being attached to the 5'-end of the first hybridizing oligonucleotide and having any nucleic acid sequence which does not hybridize to the miRNA;

deactivating the reverse transcriptase and melting a DNA produced by the reverse transcribing, thereby preparing a single-stranded cDNA reverse-transcribed from the poly(A)-tailed miRNA;

extending the single-stranded cDNA using a DNA polymerase and an extension primer longer than the reverse transcription primer, in which the extension primer is composed of a second hybridizing oligonucleotide and a second adaptor oligonucleotide, the second hybridizing oligonucleotide being capable of hybridizing specifically to a portion of the single-stranded cDNA reverse-transcribed from the poly(A)-tailed miRNA, the portion of the single-stranded cDNA excluding a portion corresponding to the 3'-end of the poly(A)-tailed miRNA, the 3'-end of the poly(A)-tailed miRNA being hybridized to the first hybridizing oligonucleotide, and the second adaptor oligonucleotide being attached to the 5'-end of the second hybridizing oligonucleotide and having any nucleic acid sequence which does not hybridize to the single-stranded cDNA; and performing PCR amplification using as a template a double-strand cDNA produced by the extending and using a reverse primer having the same nucleic acid sequence as that of the reverse transcription primer or the first adaptor oligonucleotide, and a forward primer having a sequence within the sequence of the second adaptor oligonucleotide.

DETAILED DESCRIPTION OF INVENTION

Figure 1:
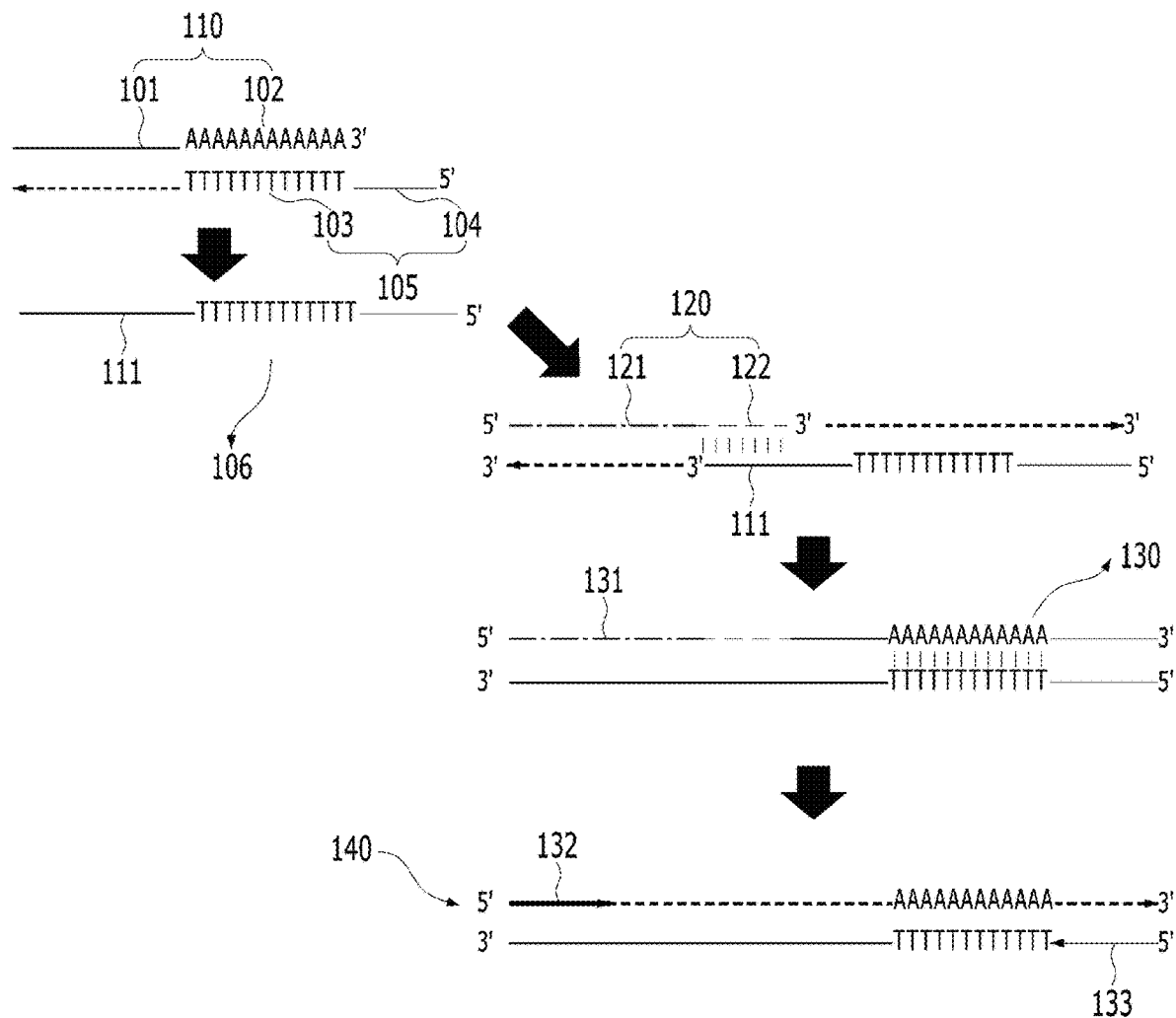
FIG. 1 is a schematic view illustrating a method of detecting miRNA using a poly(A) polymerase according to one embodiment of the present invention.

Hereinafter, the terms used herein will be defined.

As used herein, the term "nucleotide" refers to the monomeric unit of nucleic acid, which is composed of bases, pentose and phosphate. For DNA, the bases are adenine, guanine, cytosine, and thymine, and for RNA, uracil is substituted for thymine. For DNA, the pentose is 2'-deoxyribose, and for RNA, the pentose is ribose.

As used herein, the term "oligonucleotide" generally refers to a polymer of nucleotide monomer units, which is a short single-stranded nucleic acid molecule composed of 13 to 25 nucleotides. In some cases, the term may refer to a nucleic acid molecule composed of less than 13 nucleotides, including 6-mer, 7-mer, 8-mer, 9-mer, 10-mer, 11-mer and 12-mer, or more than 25 nucleotides.

As used herein, the term "polynucleotide" generally refers to a polymer of nucleotide units, which is longer than the oligonucleotide as defined above, but may also be used interchangeably with the term "oligonucleotide". Polynucleotides include both single-stranded and double-stranded nucleic acid molecules.

As used herein, the term "sense strand" refers to one single strand of a double-stranded DNA molecule, which is oriented in the same direction as the direction in which the gene of interest is read (5'-to-3' direction), and the term "antisense strand" refers to the other single strand complementary to the sense strand. However, regardless of the direction in which the gene is read, a strand whose nucleic acid sequence is first known may also be defined as "sense strand", and a strand complementary thereto may be defined as "antisense strand".

As used herein, the term "PCR (polymerase chain reaction)" or "nucleic acid amplification reaction" refers to a reaction that amplifies a certain target nucleic acid molecule using a heat-stable DNA polymerase. PCR is performed using a reaction buffer containing, in addition to the DNA polymerase, oligonucleotide primers (forward and reverse primers) capable of hybridizing specifically to a target nucleic acid, a deoxynucleotide (dNTP) mixture, divalent ions such as $Mg^{2+}$, and the like. A DNA molecule produced by the PCR reaction is herein referred to as "amplification product".

As used herein, the term "primer extension" refers to a non-chain reaction in which a template nucleic acid having a limited length is extended using a DNA polymerase and primers complementary thereto and which is terminated at the 5'-end of the template nucleic acid. A DNA molecule produced by the primer extension is herein referred to as "extension product".

As used herein, the term "primer" refers to an oligonucleotide or polynucleotide that hybridizes complementarily to template DNA and that is used to initiate PCR reaction or primer extension. PCR reaction is performed using a forward primer (or a sense primer) selected from a sense strand which is oriented in the same direction as the direction in which a nucleic acid molecule to be amplified is read, and a reverse primer (or an antisense primer) selected from an antisense strand complementary to the sense strand. Primer extension is generally performed using a single extension primer.

As used herein, the term "adaptor" refers to either an oligonucleotide which is added to the 5'-end of sense DNA corresponding to a certain miRNA in order to specifically recognize the miRNA, or an oligonucleotide which is added to the 5'-end of a reverse transcription primer for reverse transcription of miRNA. In this case, the adaptor may be used as a primer sequence to amplify extended cDNA, and in the latter case, the adaptor may be used to calibrate a low Tm value which appears when the primer consists only of a nucleic acid sequence capable of hybridizing to miRNA. The adaptor may be designed to have no homology to a template nucleic acid to be amplified and other primers, except for an oligonucleotide primer for extension, and thus may be designed so as to minimize nonspecific amplification.

As used herein, the term "hybridizing oligonucleotide" refers to a nucleic acid molecule capable of hybridizing complementarily to either miRNA or cDNA reverse-transcribed from the miRNA.

As used herein, the term "universal primer" refers to a primer enabling any kind of nucleic acid to be amplified. The universal primer may be prepared using the nucleic acid sequence of an adaptor oligonucleotide added for reverse transcription and primer extension. In this case, there is an advantage in that a single primer set may be used, thereby reducing the production cost of the kit.

As used herein, the term "forward primer" refers to a primer oriented in the same direction in which the gene of interest is read (5'-to-3' direction). On the contrary, the term "reverse primer" refers to a primer oriented opposite to a direction in which the gene of interest is read.

In accordance with one aspect of the present invention, there is provided a kit for detecting miRNA, comprising:

a short reverse transcription primer composed of a first hybridizing oligonucleotide and a first adaptor oligonucleotide, the first hybridizing oligonucleotide having a nucleic acid sequence which hybridizes specifically to the 3'-end of a miRNA or the 3'-end of a poly(A)-tailed miRNA obtained by tailing a miRNA with poly(A) using a poly(A) polymerase, and the first adaptor oligonucleotide being attached to the 5'-end of the first hybridizing oligonucleotide and having any nucleic acid sequence which does not hybridize to the miRNA;

an extension primer longer than the reverse transcription primer and composed of a second hybridizing oligonucleotide and a second adaptor oligonucleotide, the second hybridizing oligonucleotide being capable of hybridizing specifically to a portion of a single-stranded cDNA reverse-transcribed from the miRNA or the poly(A)-tailed miRNA, the portion of the single-stranded cDNA excluding a portion corresponding to the 3'-end of the miRNA or the poly(A)-tailed miRNA, the 3'-end of the miRNA or the poly(A)-tailed miRNA being hybridized to the first hybridizing oligonucleotide, and the second adaptor oligonucleotide being attached to the 5'-end of the second hybridizing oligonucleotide and having any nucleic acid sequence which does not hybridize to the single-stranded cDNA; and a forward primer having a sequence within the sequence of the second adaptor oligonucleotide.

The kit may further comprise a reverse primer composed of the same nucleic acid sequence as that of the first adaptor oligonucleotide, in which the reverse primer may be a universal reverse primer having a constant nucleic acid sequence regardless of the kind of miRNA.

In the kit, the forward primer may be a universal forward primer having a constant nucleic acid sequence regardless of the kind of miRNA.

In the kit, the first hybridizing oligonucleotide that hybridizes specifically to the 3'-end of the miRNA may be about 3 to 12 nt in length, and the first adaptor oligonucleotide may be about 3 to 30 nt, for example about 20 to 22 nt, about 17 to 22 nt, or about 12 to 22 nt in length. In this case, the short reverse transcription primer may be about 26 to 28 nt, about 23 to 28 nt, or about 18 to 28 nt, preferably about 18 to 28 nt in length. In the kit, the second adaptor oligonucleotide may be about 32 to 61 nt or about 56 to 63 nt in length, and its length is adjustable according to the kind of miRNA.

In the kit, the first hybridizing oligonucleotide which hybridizes specifically to the 3'-end of the poly(A)-tailed miRNA may be about 12 to 30 nt in length, and the first adaptor oligonucleotide may be about 3 to 30 nt, preferably about 17 to 22 nt in length. In this case, the short reverse transcription primer may be about 29 to 34 nt in length. In the kit, the second adaptor oligonucleotide may be about 32 to 61 nt or about 56 to 63 nt in length, and its length is adjustable according to the kind of miRNA.

The kit may further comprise a reverse transcriptase, a heat-stable DNA polymerase, and a dNTP mixture, and may also further comprise a poly(A) polymerase and ATP.

In accordance with another aspect of the present invention, there is provided a method for detecting miRNA, comprising:

reverse-transcribing a miRNA using a reverse transcriptase and a short reverse transcription primer, in which the short reverse transcription primer is composed of a first hybridizing oligonucleotide and a first adaptor oligonucleotide, the first hybridizing oligonucleotide having a nucleic acid sequence which hybridizes specifically to the 3'-end of the miRNA, and the first adaptor oligonucleotide being attached to the 5'-end of the first hybridizing oligonucleotide and having any nucleic acid sequence which does not hybridize to the miRNA;

deactivating the reverse transcriptase and melting a DNA produced by the reverse transcription, thereby preparing a single-stranded cDNA reverse-transcribed from the miRNA;

extending the single-stranded cDNA using a DNA polymerase and an extension primer longer than the reverse transcription primer, in which the extension primer is composed of a second hybridizing oligonucleotide and a second adaptor oligonucleotide, the second hybridizing oligonucleotide being capable of hybridizing specifically to a portion of the single-stranded cDNA reverse-transcribed from the miRNA, the portion of the single-stranded cDNA excluding a portion corresponding to the 3'-end of the miRNA, the 3'-end of the miRNA being hybridized to the first hybridizing oligonucleotide, and the second adaptor oligonucleotide being attached to the 5'-end of the second hybridizing oligonucleotide and having any nucleic acid sequence which does not hybridize to the single-stranded cDNA; and performing PCR amplification using as a template a double-strand cDNA produced by the extending and using a reverse primer having the same nucleic acid sequence as that of the reverse transcription primer or the first adaptor oligonucleotide, and a forward primer having a sequence within the sequence of the second adaptor oligonucleotide.

In the detection method, the forward primer may be a universal forward primer having a constant nucleic acid sequence regardless of the kind of miRNA. The first hybridizing oligonucleotide may be about 3 to 12 nt in length, and the first adaptor oligonucleotide may be about 3 to 30 nt, for example about 20 to 22 nt, about 17 to 22 nt, or about 12 to 22 nt in length. In this case, the short reverse transcription primer may be about 26 to 28 nt, about 23 to 28 nt, or about 18 to 28 nt, preferably about 18 to 28 nt in length. In the method, the second adaptor oligonucleotide may be about 32 to 61 nt or about 56 to 63 nt in length, and its length is adjustable according to the kind of miRNA. The PCR amplification may be performed by real-time PCR reaction.

In accordance with still another aspect of the present invention, there is provided a method for detecting miRNA, comprising:

tailing a miRNA with poly(A) using a poly(A) polymerase, thereby preparing a poly(A)-tailed miRNA;

reverse-transcribing the poly(A)-tailed miRNA using a reverse transcriptase and a short reverse transcription primer, in which the short reverse transcription primer is composed of a first hybridizing oligonucleotide and a first adaptor oligonucleotide, the first hybridizing oligonucleotide being composed of poly dT which hybridizes specifically to the poly(A) tail of the poly(A)-tailed miRNA, and the first adaptor oligonucleotide being attached to the 5'-end of the first hybridizing oligonucleotide and having any nucleic acid sequence which does not hybridize to the miRNA;

deactivating the reverse transcriptase and melting a DNA produced by the reverse transcribing, thereby preparing a single-stranded cDNA reverse-transcribed from the poly(A)-tailed miRNA;

extending the single-stranded cDNA using a DNA polymerase and an extension primer longer than the reverse transcription primer, in which the extension primer is composed of a second hybridizing oligonucleotide and a second adaptor oligonucleotide, the second hybridizing oligonucleotide being capable of hybridizing specifically to a portion of the single-stranded cDNA reverse-transcribed from the poly(A)-tailed miRNA, the portion of the single-stranded cDNA excluding a portion corresponding to the 3'-end of the poly(A)-tailed miRNA, the 3'-end of the poly(A)-tailed miRNA being hybridized to the first hybridizing oligonucleotide, and the second adaptor oligonucleotide being attached to the 5'-end of the second hybridizing oligonucleotide and having any nucleic acid sequence which does not hybridize to the single-stranded cDNA; and performing PCR amplification using as a template a double-strand cDNA produced by the extending and using a reverse primer having the same nucleic acid sequence as that of the reverse transcription primer or the first adaptor oligonucleotide, and a forward primer having a sequence within the sequence of the second adaptor oligonucleotide.

In the detection method, the forward primer may be a universal forward primer having a constant nucleic acid sequence regardless of the kind of miRNA, and the reverse primer may be a universal reverse primer having a constant nucleic acid sequence regardless of the kind of miRNA. The first hybridizing oligonucleotide may be about 12 to 30 nt in length, and the first adaptor oligonucleotide may be about 3 to 30 nt, preferably about 17 to 22 nt in length. In this case, the short reverse transcription primer may be about 29 to 34 nt in length. In the method, the second adaptor oligonucleotide may be about 32 to 61 nt or about 56 to 63 nt in length, and its length is adjustable according to the kind of miRNA. The PCR amplification may be performed by real-time PCR reaction.

Unless otherwise specified herein, a nucleic acid molecule composed of a plurality of oligonucleotides and/or polynucleotides is read from the 5'-end to the 3'-end.

Hereinafter, a kit and method according to one embodiment of the present invention will be described in further detail with reference to the accompanying drawings.

FIG. 1 is a schematic view illustrating a method of detecting miRNA using a poly(A) polymerase according to one embodiment of the present invention. As shown in FIG. 1, miRNA 101 is a very short nucleic acid molecule which is about 22 nt in length. The miRNA 101 has no poly(A) tail, unlike mRNA. For this reason, when a poly(A) polymerase and ATP are mixed and reacted with a sample containing the miRNA 101, a poly(A) tail 102 (SEQ ID NO: 20) is then attached to the miRNA 101 to produce a poly(A)-tailed miRNA 110. When a short reverse transcription primer 105 composed of poly dT (SEQ ID NO: 21) (i.e. a first hybridizing oligonucleotide 103) and a first adaptor oligonucleotide 104, is added to the miRNA 110, the first hybridizing oligonucleotide 103 then binds complementarily to the poly(A) tail. When a reverse transcriptase and a dNTP mixture is added to the miRNA complex and a reverse transcription reaction is performed, a reverse transcription product 106 of the target miRNA is produced which consists of the first adaptor oligonucleotide 104, the first hybridizing oligonucleotide 103 and an antisense strand cDNA 111. Then, the reverse transcriptase is deactivated and the DNA is melted, thereby ensuring that the reverse transcription process is terminated, thereby preparing a single-stranded cDNA. Then, an extension primer 120 (longer than the reverse transcription primer), which has at the 3'-end a second hybridizing oligonucleotide 122 having a sequence complementary to the antisense strand cDNA and at the 5'-end a second adaptor oligonucleotide 121 having any nucleic acid sequence that does not hybridize to both of the miRNA 110 and the antisense strand cDNA 111, is hybridized to the reverse transcription product 106. Then, the reverse transcription product 106 is subjected to primer extension with a DNA polymerase, thereby producing an extended double-stranded cDNA 130. The sense strand of the extended double-stranded cDNA 130 is indicated by reference numeral 131. Using the extended double-stranded cDNA 130 as a template, a PCR reaction is performed using a reverse primer 133 having a nucleic acid sequence identical with that of the first adaptor oligonucleotide and a forward primer 132 having a nucleic acid sequence of the 5'-end of the second adaptor oligonucleotide, thereby producing a PCR product 140. Here, the extended double-stranded cDNA 130 is exponentially amplified.

Figure 2:
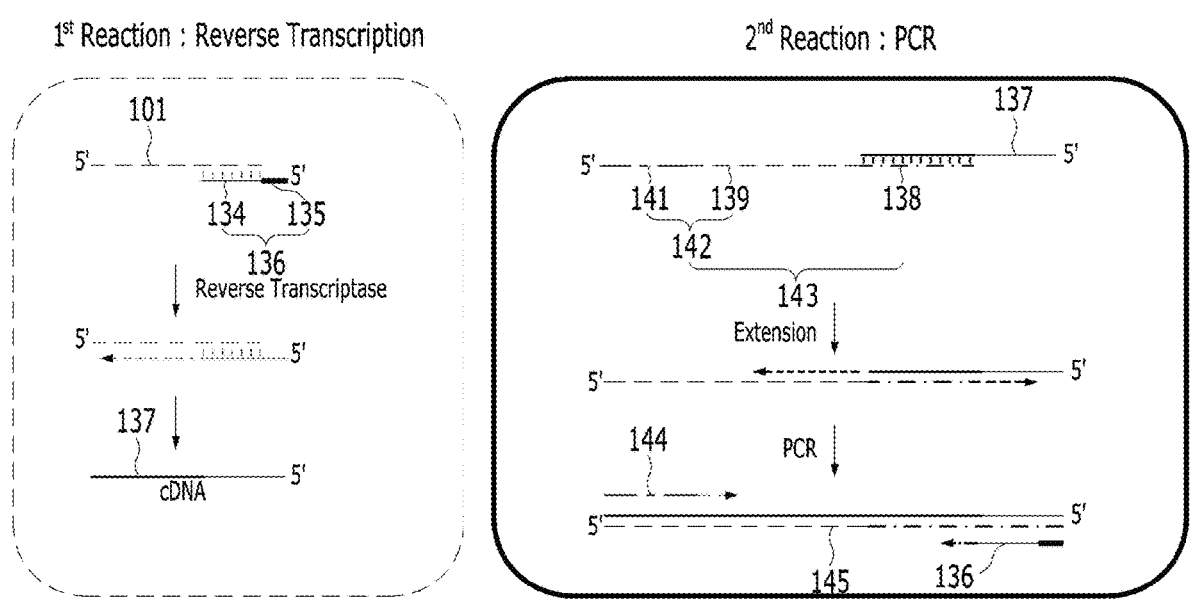
FIG. 2 is a schematic view illustrating a method of detecting miRNA using a miRNA-specific reverse transcription primer according to one embodiment of the present invention.
Figure 3:
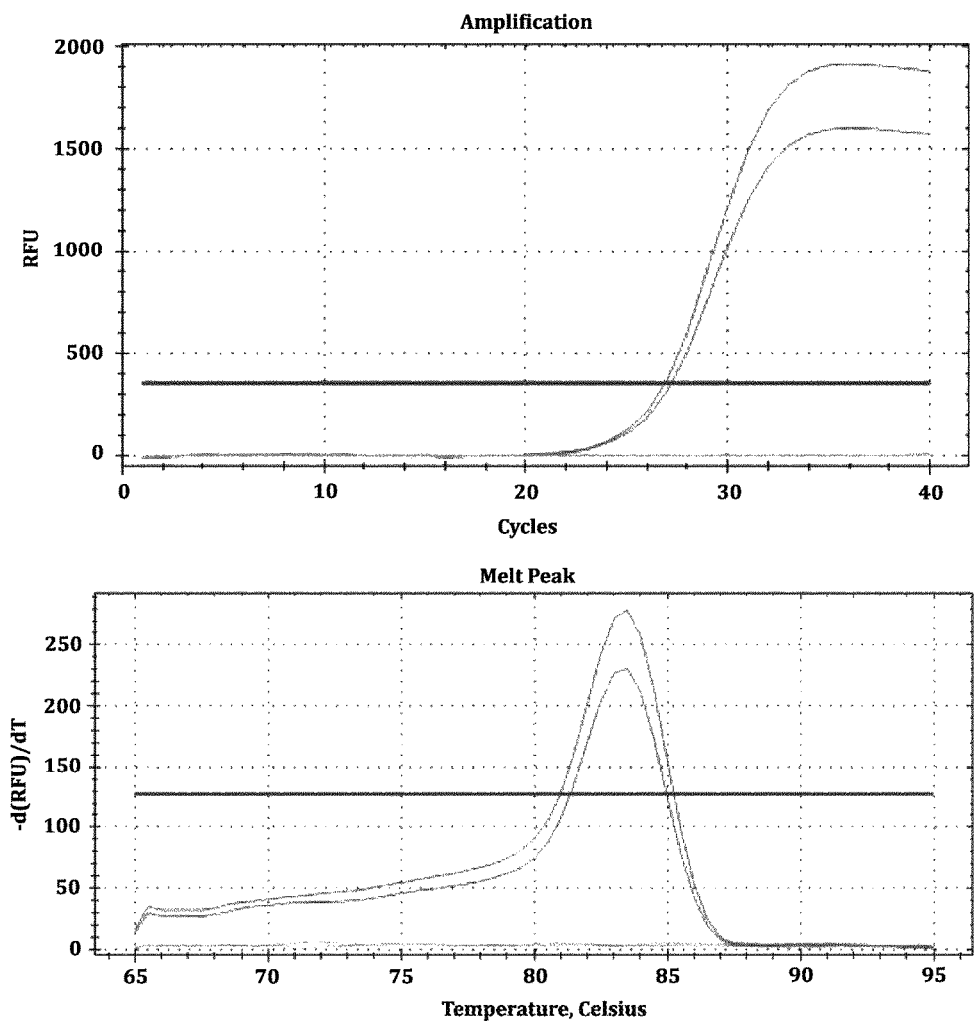
FIGS. 3 to 10 show the results of amplifying miR-532, miR-196b, miR-362, miR-29c, miR-106b, miR-200c, miR-127 and miR-145, respectively, by a miRNA detection kit and method using a poly(A) polymerase and oligo dT primers in examples of the present invention. In each of FIGS. 3 to 10, the top is a graph showing the change in fluorescence intensity as a function of the number of amplification cycles; the middle is a graph showing the change in fluorescence emission rate as a function of temperature; the table on the left side of the bottom shows the kind of sample, the threshold for fluorescence detection, and melting point; and the right side of the bottom is a photograph showing the result of 1.5% agarose gel electrophoresis.
Figure 3:
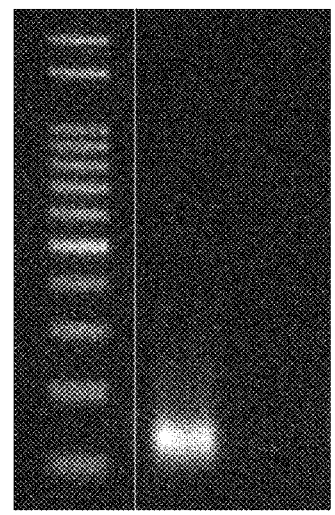
Figure 4:
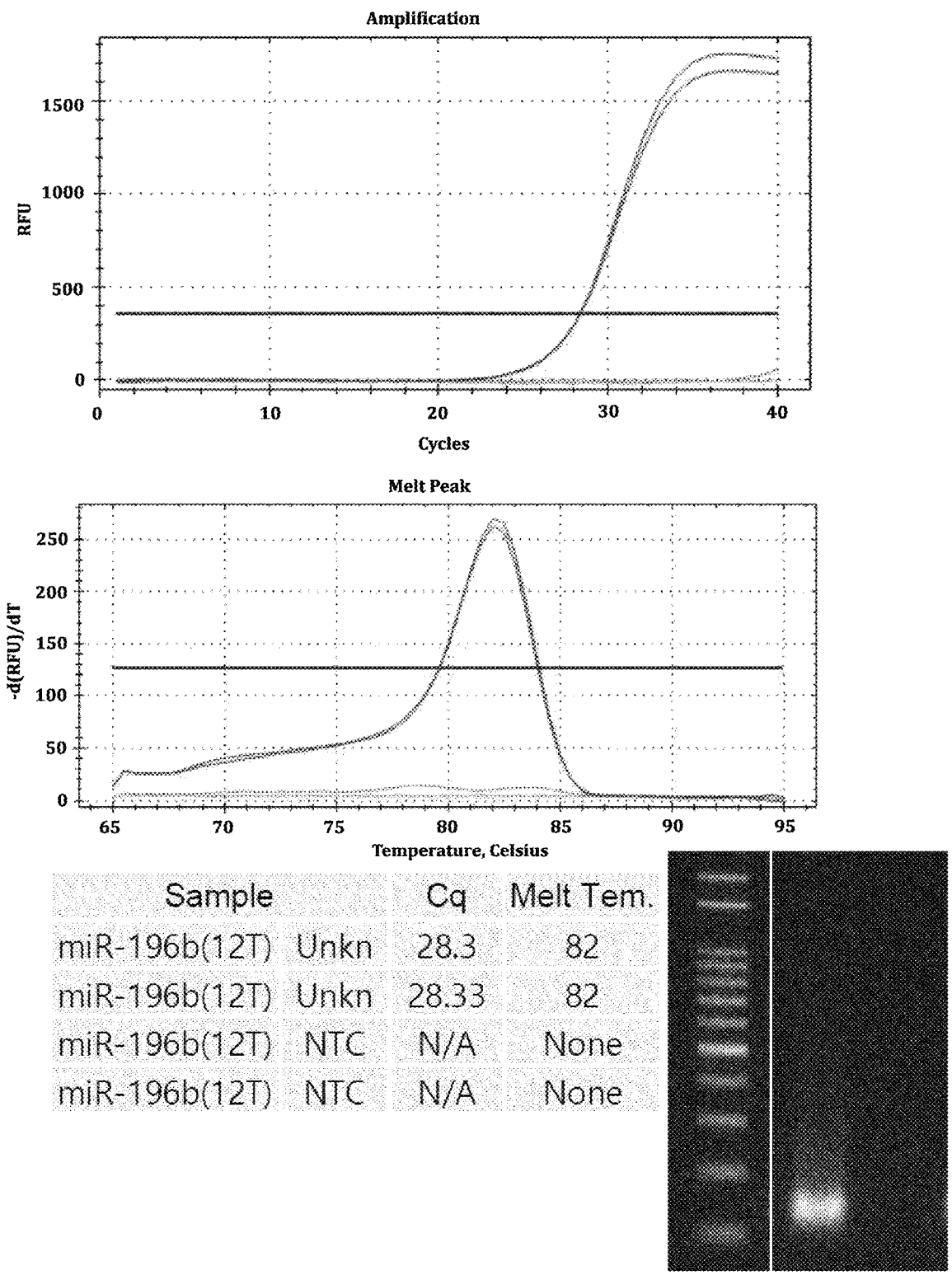
Figure 5:
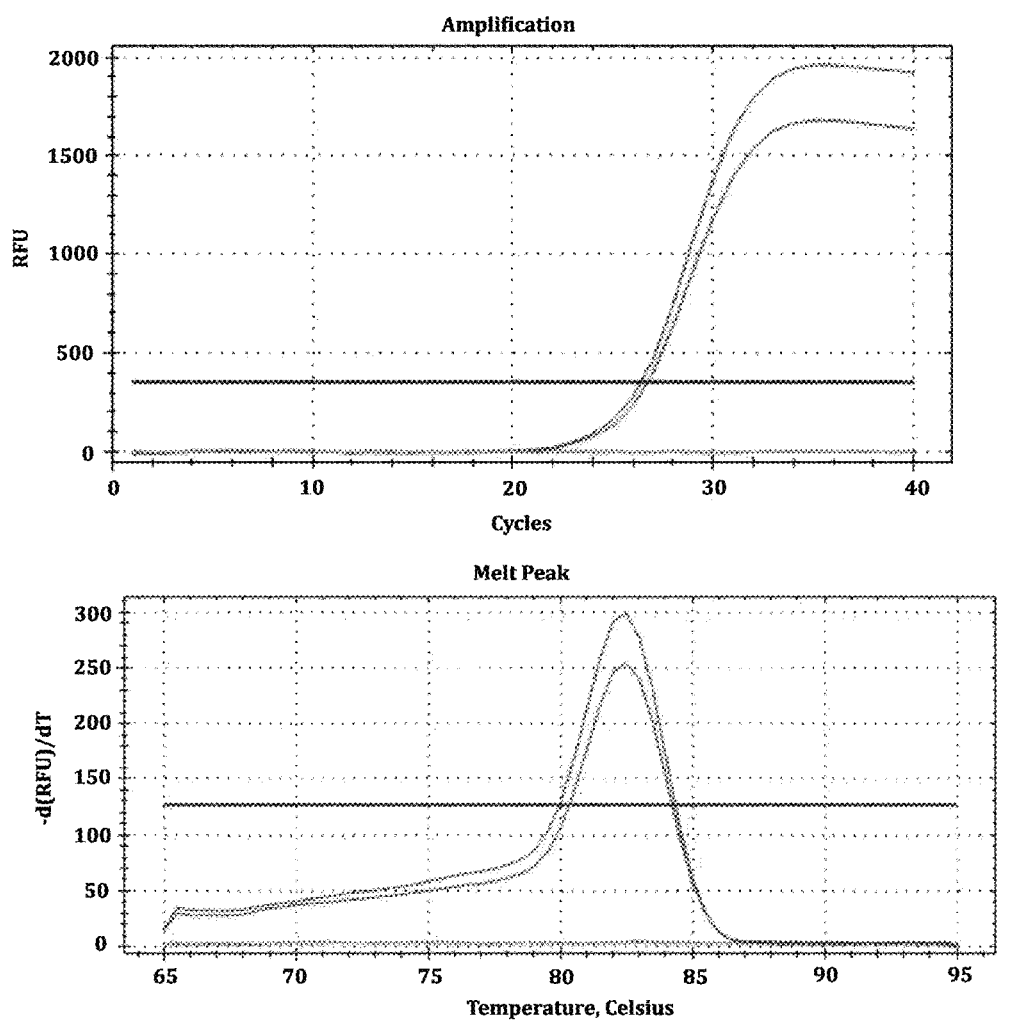
Figure 5:
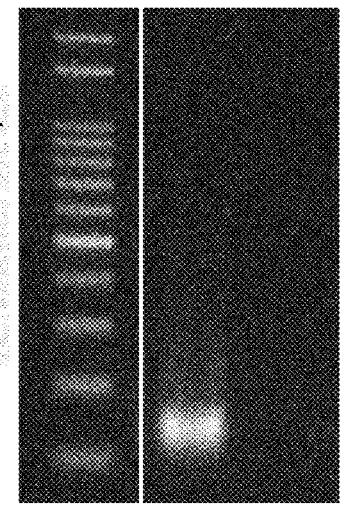
Figure 6:
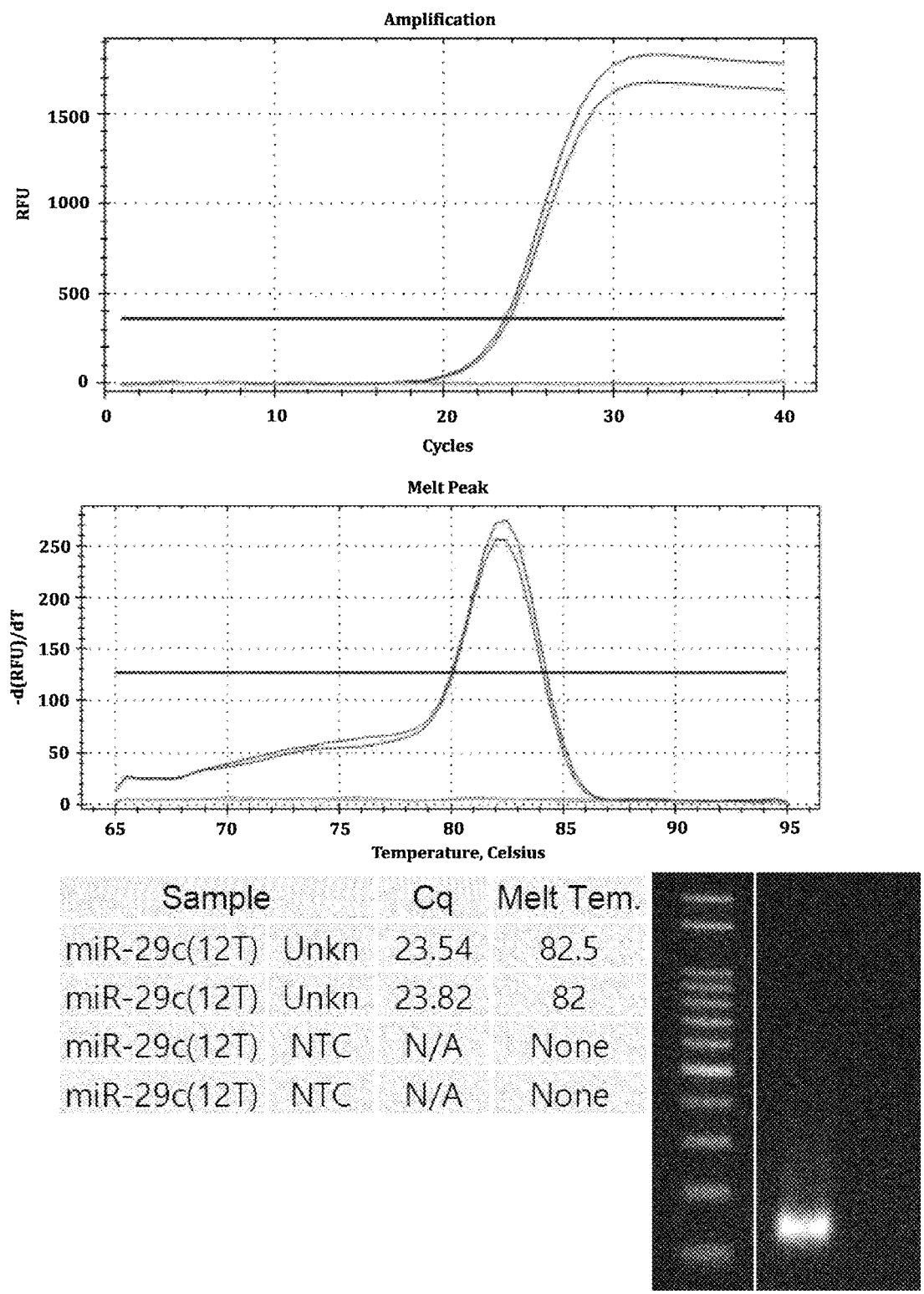
Figure 7:
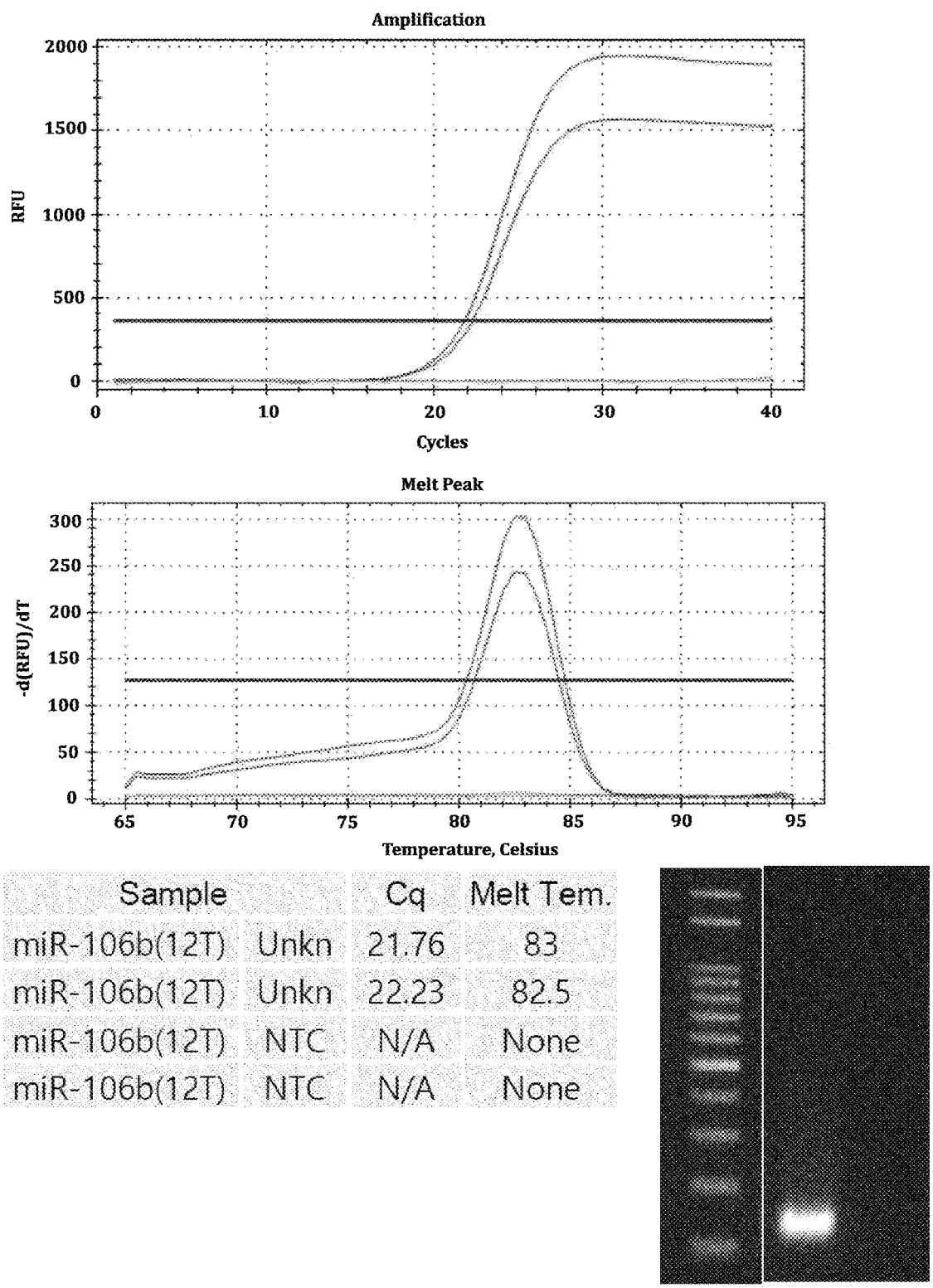
Figure 8:
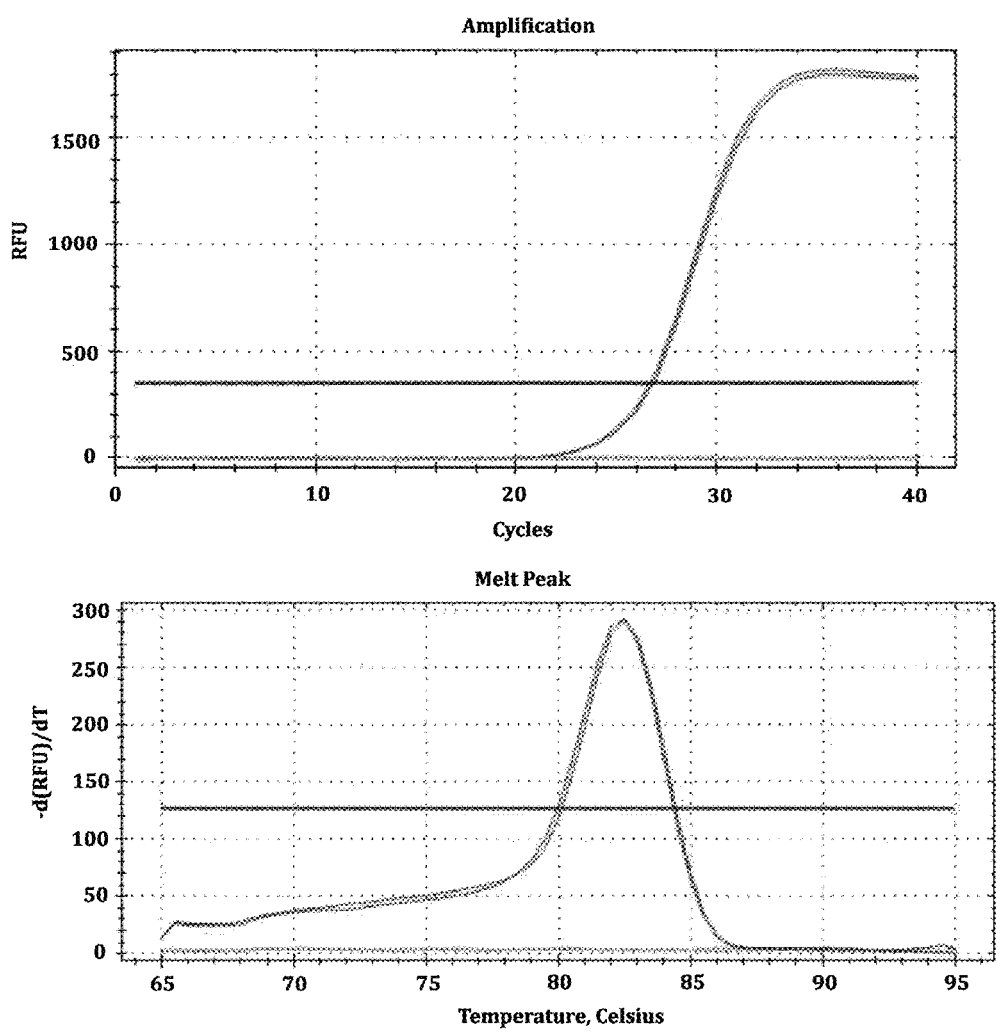
Figure 8:
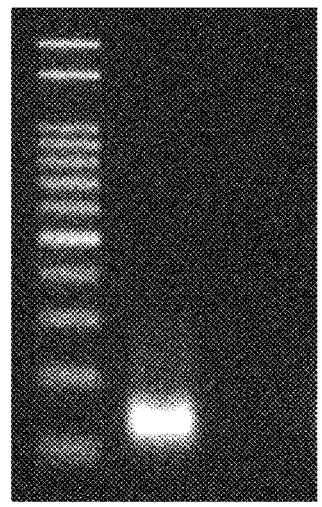
Figure 9:
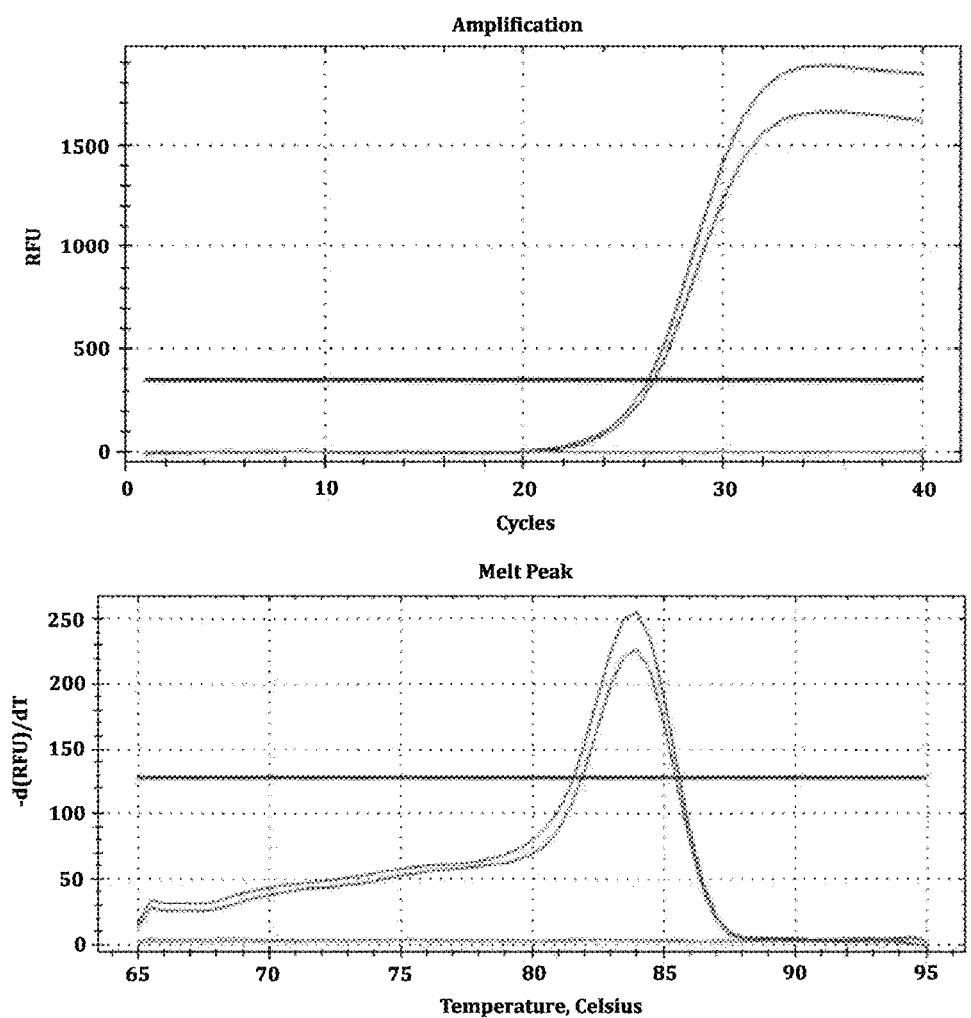
Figure 10:
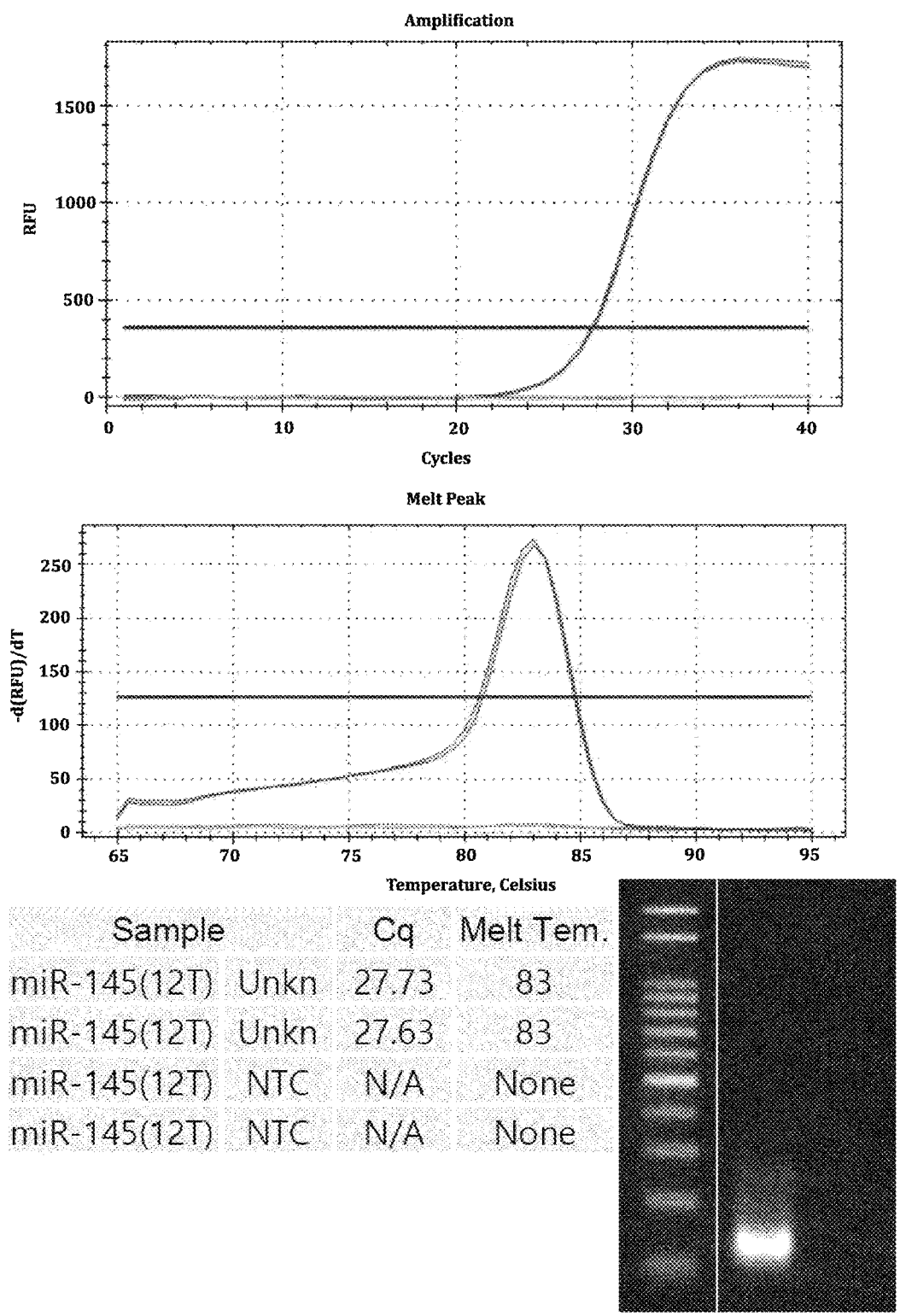
Figure 11:
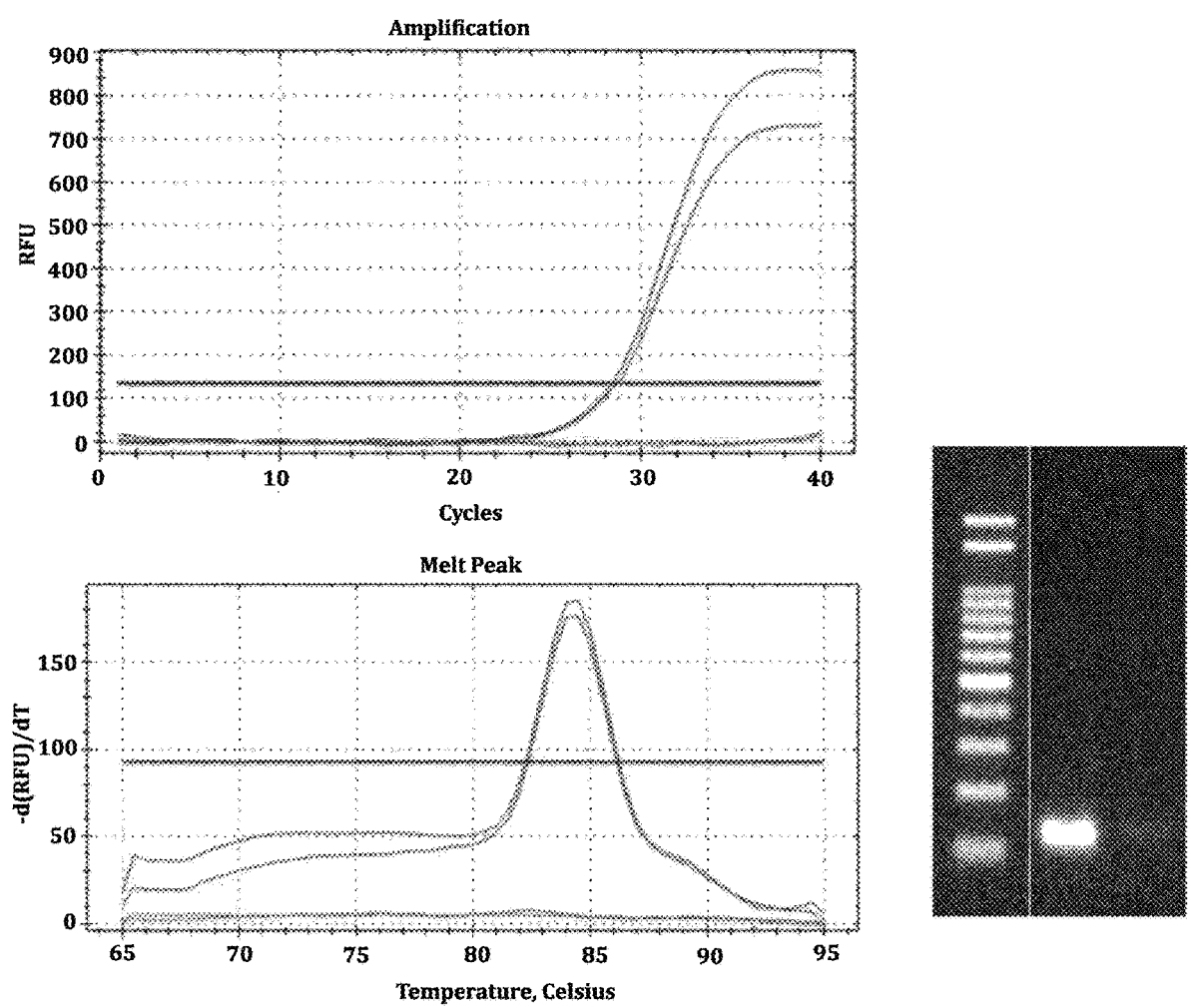
FIGS. 11 to 18 show the results of amplifying miR-532, miR-196b, miR-362, miR-29c, miR-106b, miR-200c, miR-127 and miR-145, respectively, by a miRNA detection kit and method using miRNA-specific primers (reverse transcription primers) in examples of the present invention. In each of FIGS. 11 to 18, the top is a graph showing the change in fluorescence intensity as a function of the number of amplification cycles; the left side of the middle is a graph showing the change in fluorescence emission rate as a function of temperature; the table on the bottom shows the kind of sample, the threshold for fluorescence detection, and melting point; and the right side of the middle is a photograph showing the result of 1.5% agarose gel electrophoresis.
Figure 12:
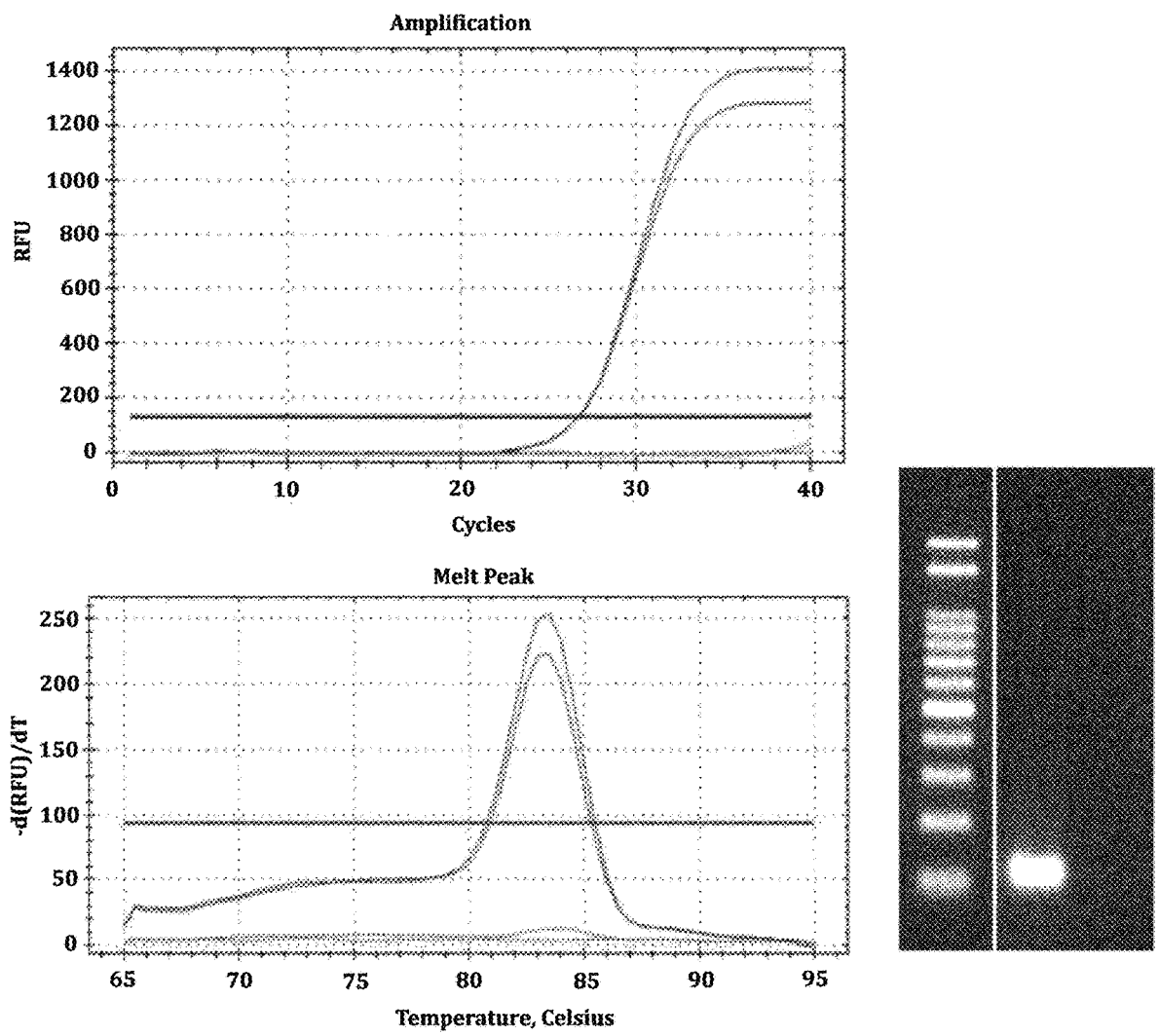
Figure 13:
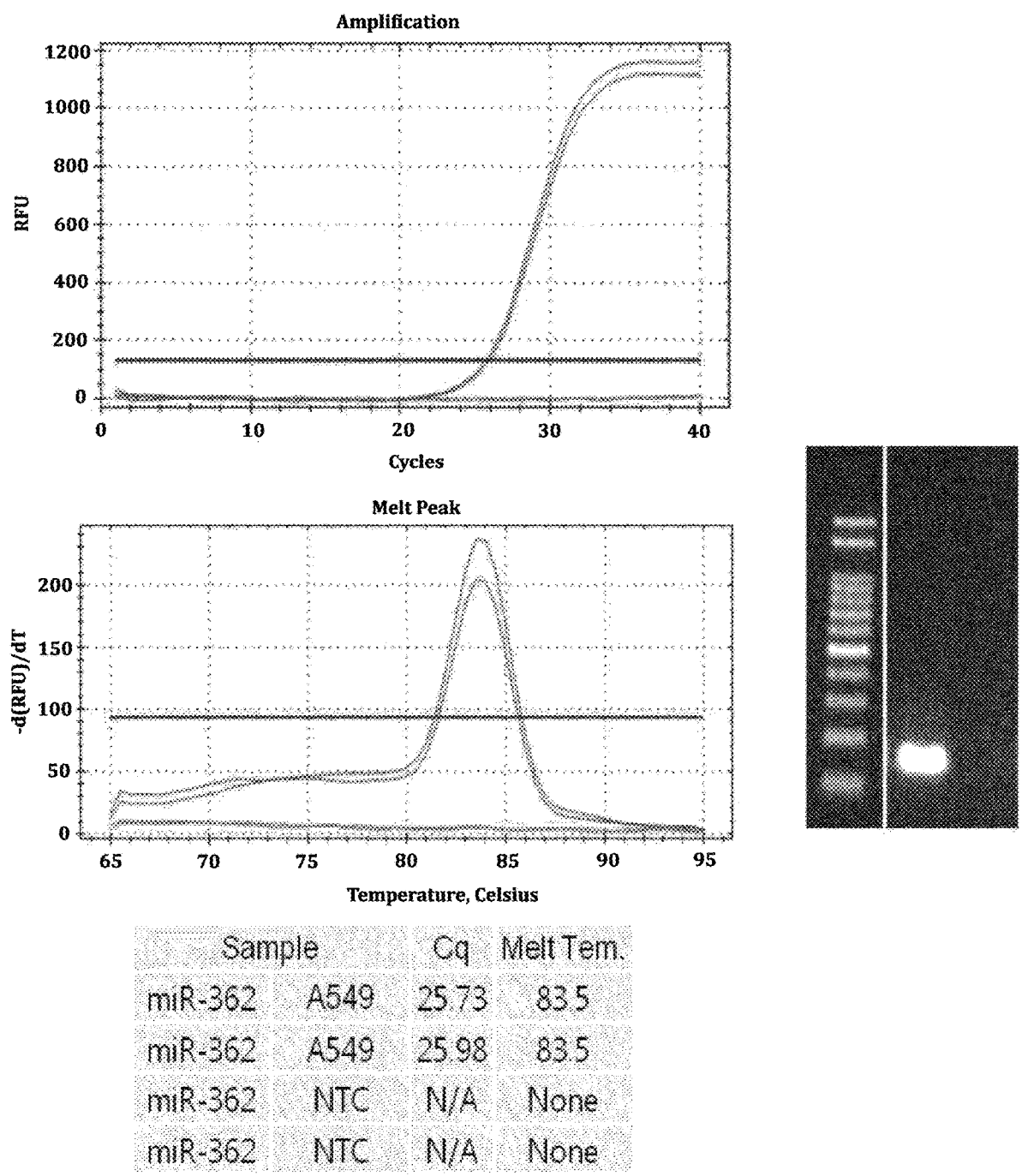
Figure 14:
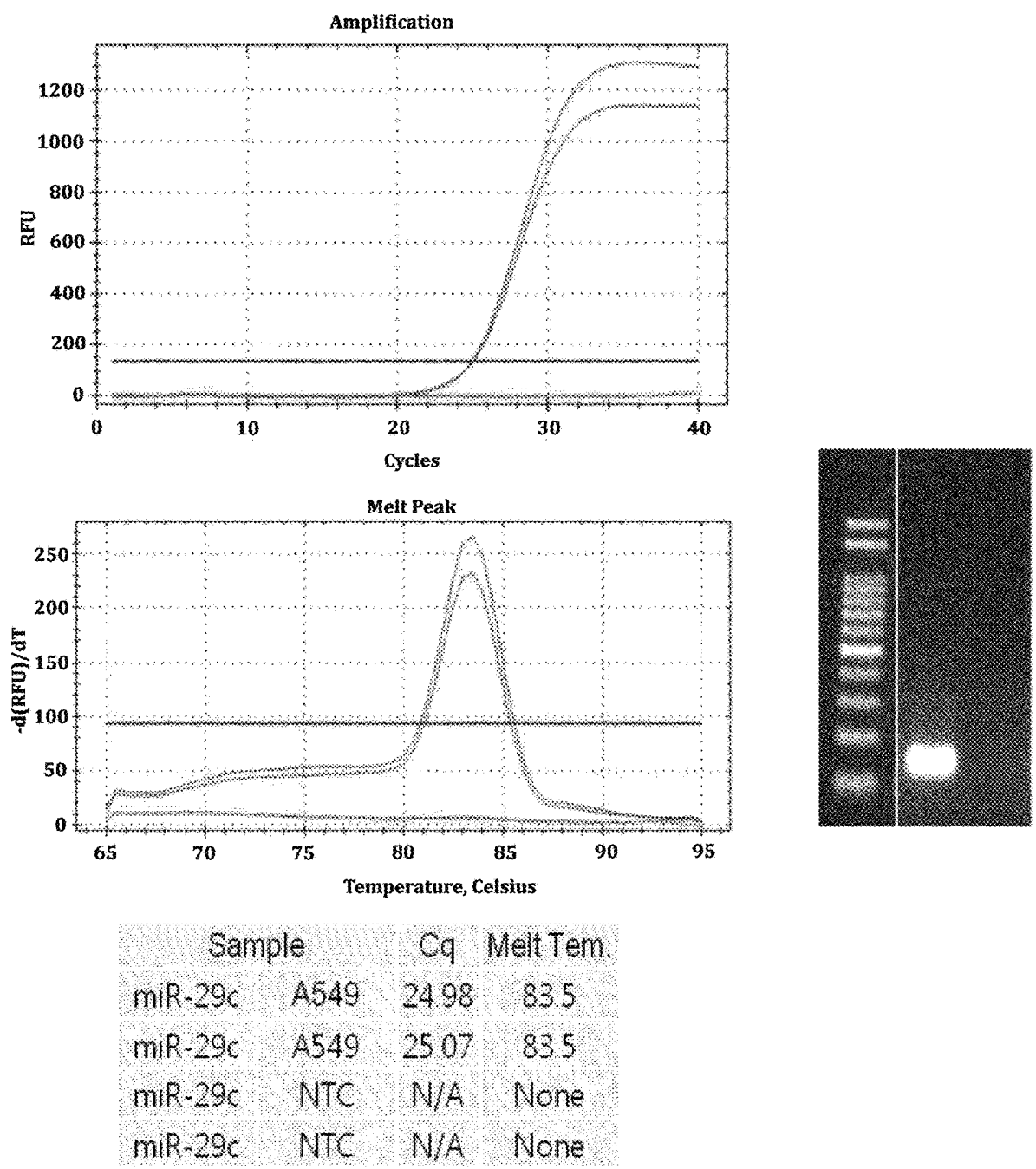
Figure 15:
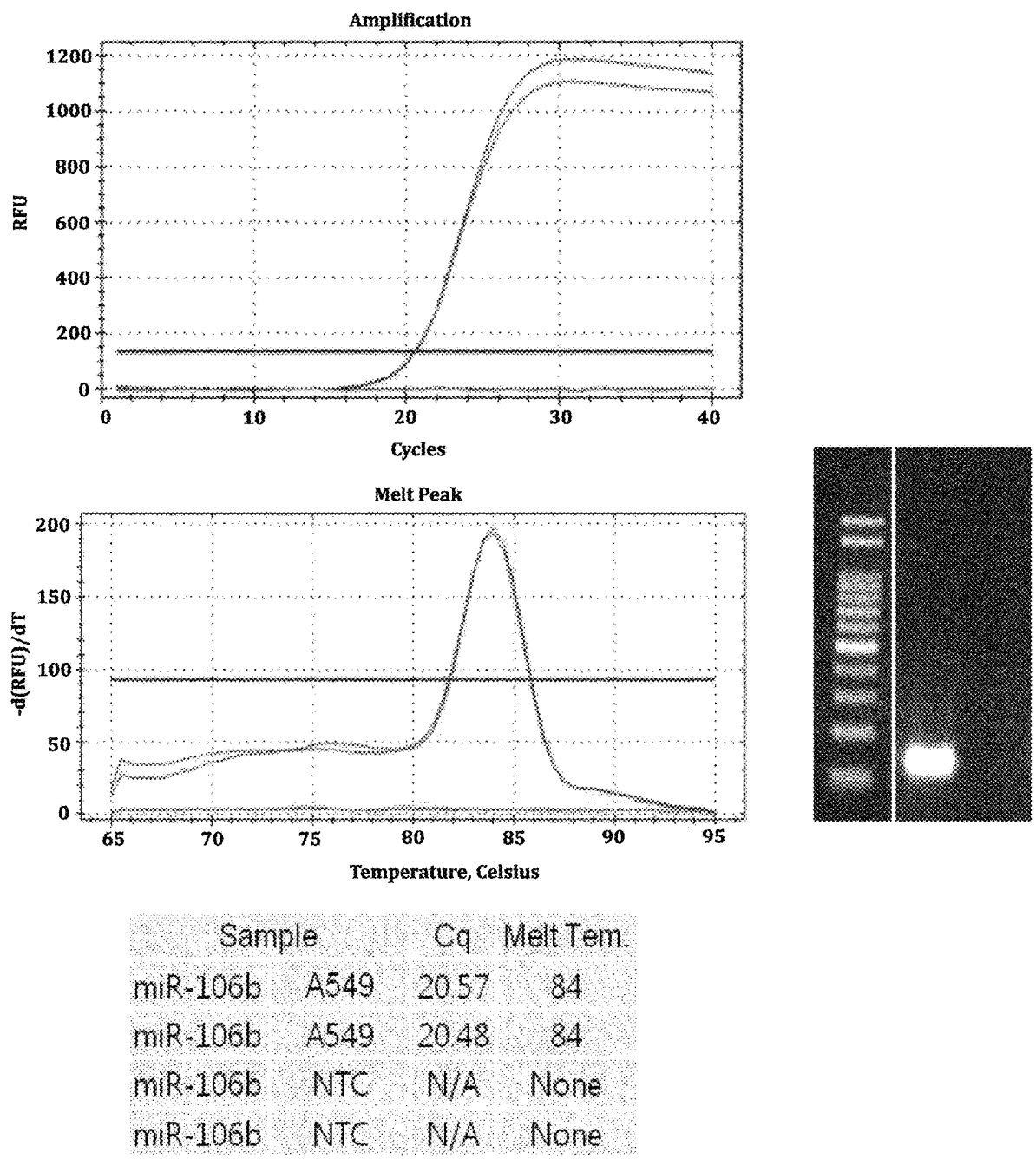
Figure 16:
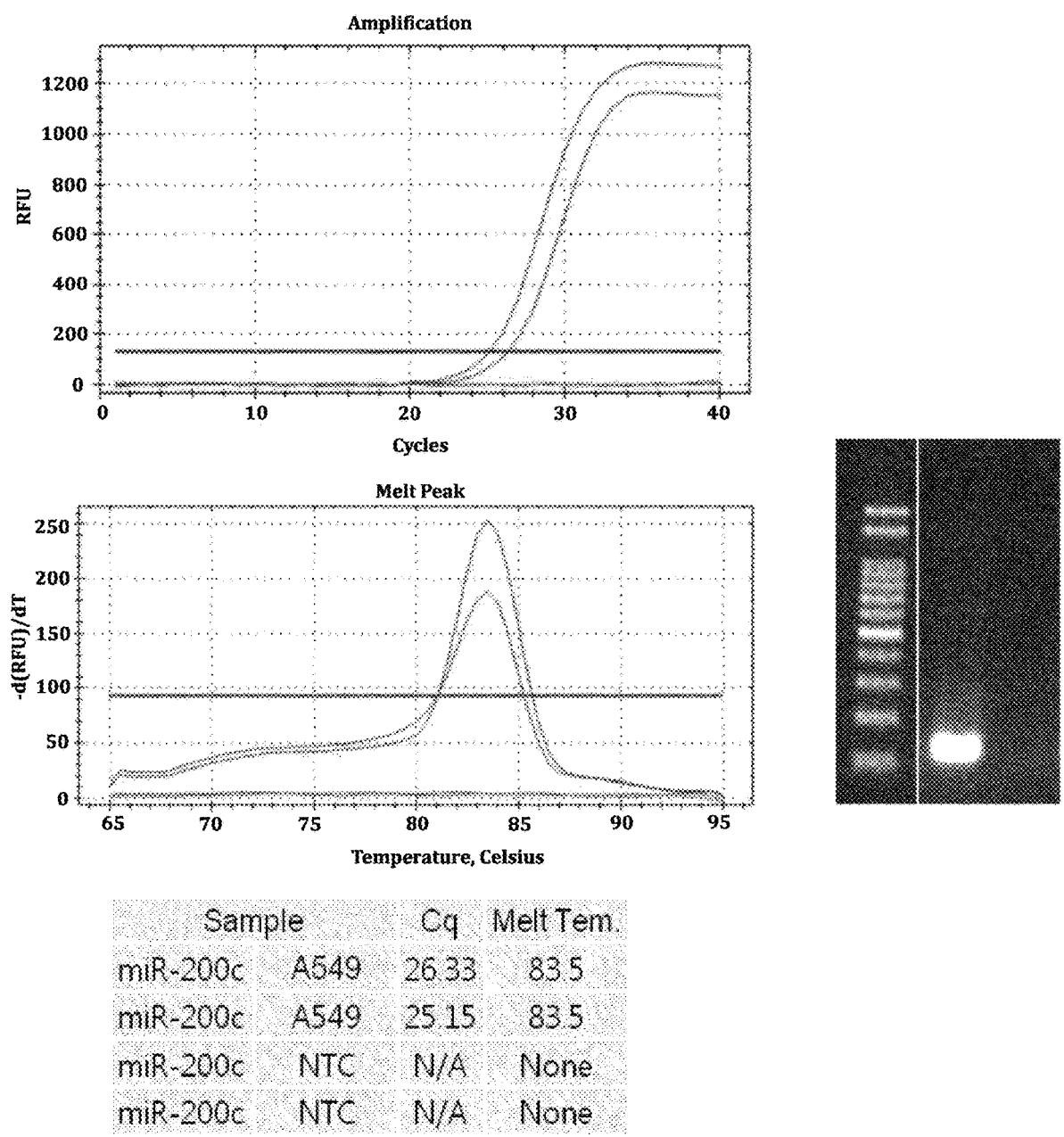
Figure 17:
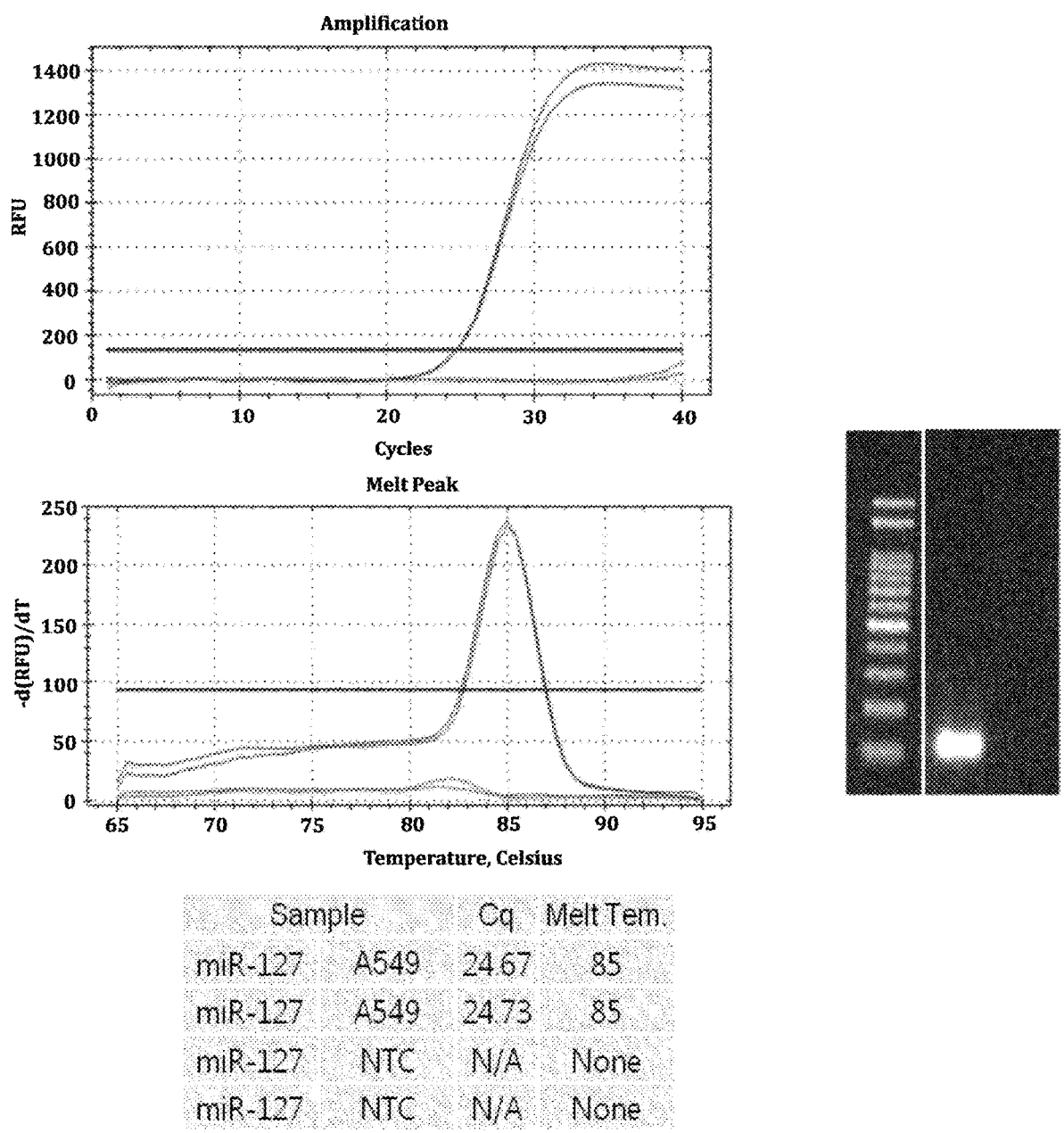
Figure 18:
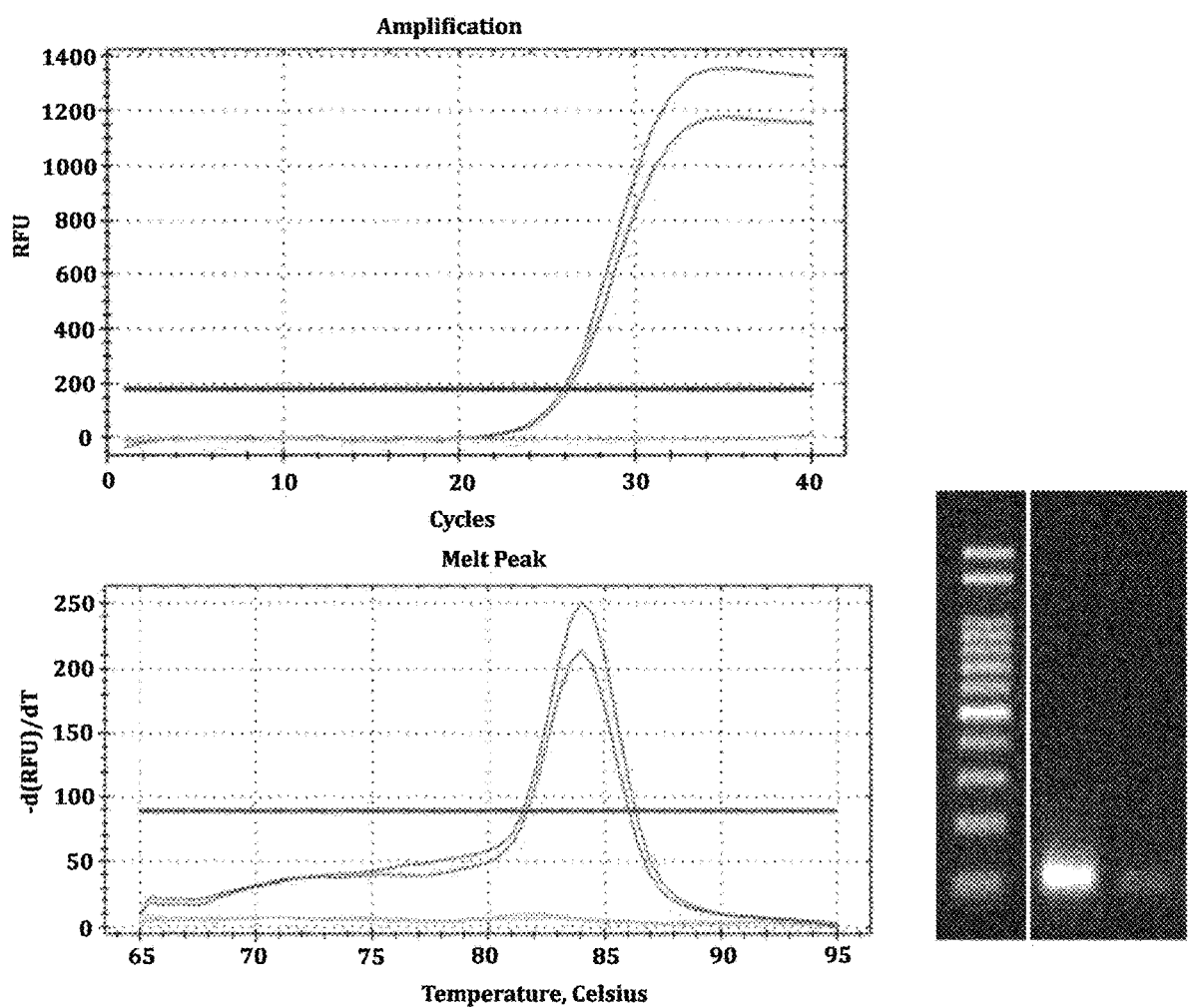
Figure 19:
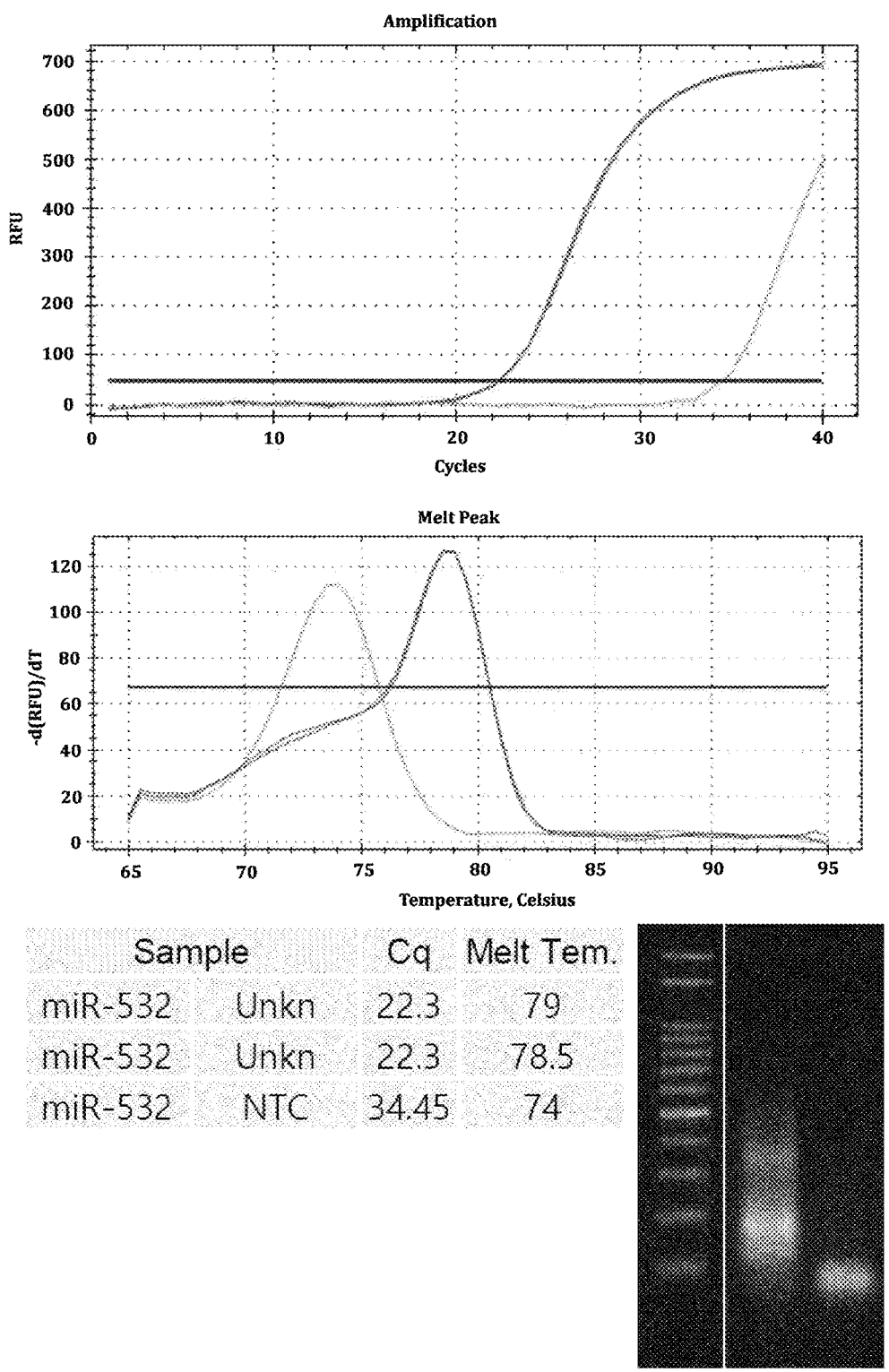
FIGS. 19 to 26 show the results of amplifying miR-532, miR-196b, miR-362, miR-29c, miR-106b, miR-200c, miR-127 and miR-145, respectively, by use of a miRNA detection kit (Qiagen) in comparative examples. In each of FIGS. 19 to 26, the top is a graph showing the change in fluorescence intensity as a function of the number of amplification cycles; the middle is a graph showing the change in fluorescence emission rate as a function of temperature; the table on the left side of the bottom shows the kind of sample, the threshold for fluorescence detection, and melting point; and the right side of the bottom is a photograph showing the result of 1.5% agarose gel electrophoresis.
Figure 20:
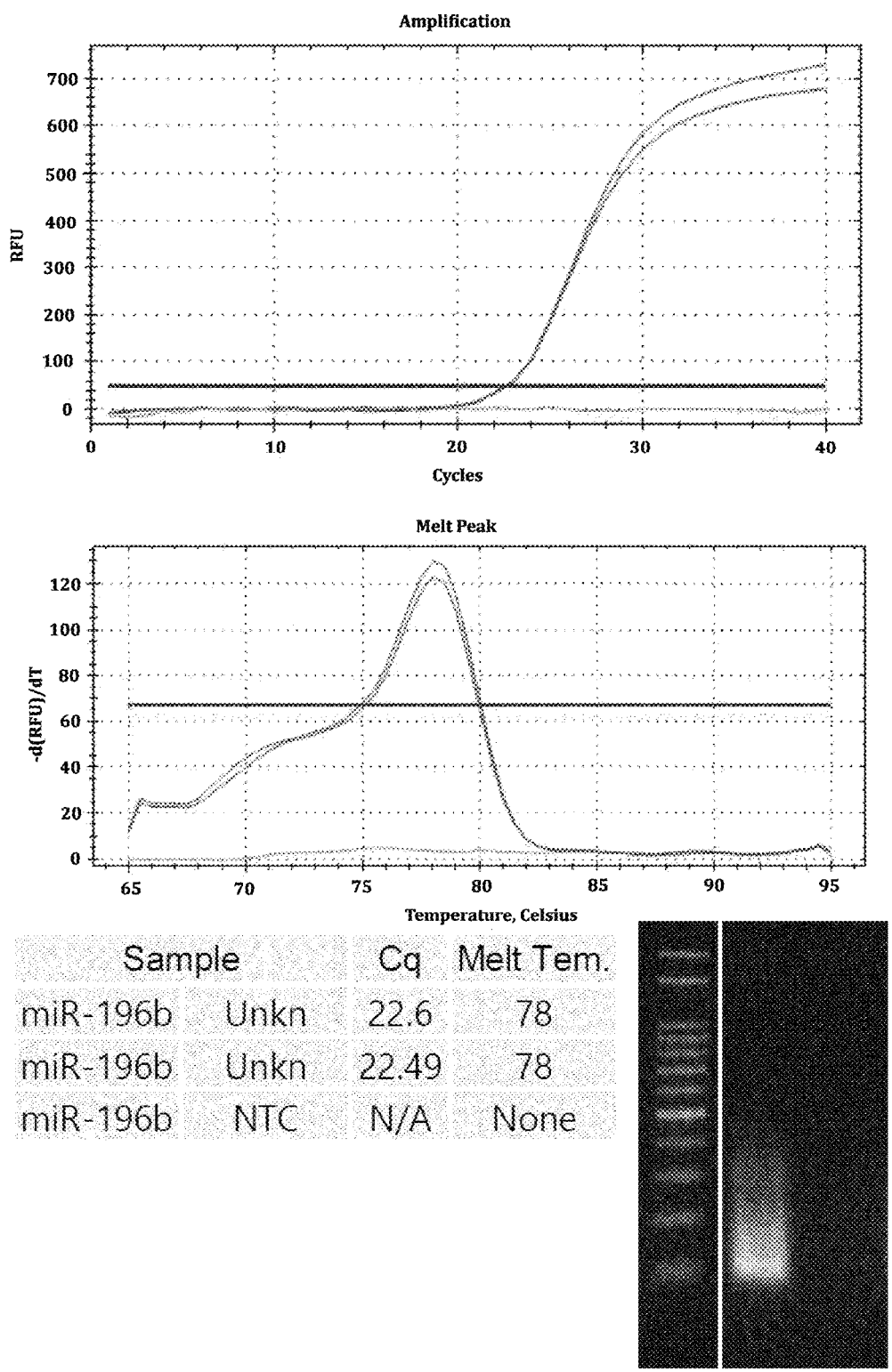
Figure 21:
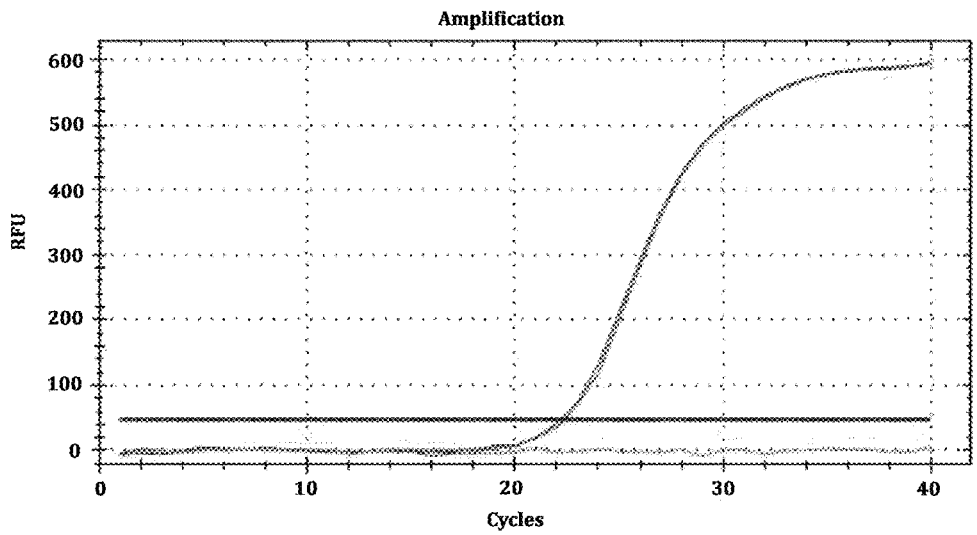
Figure 21:
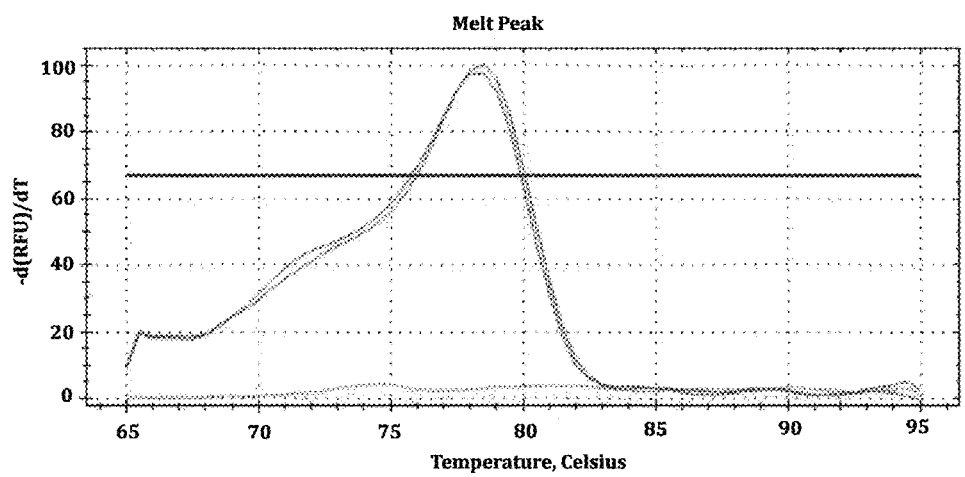
Figure 21:
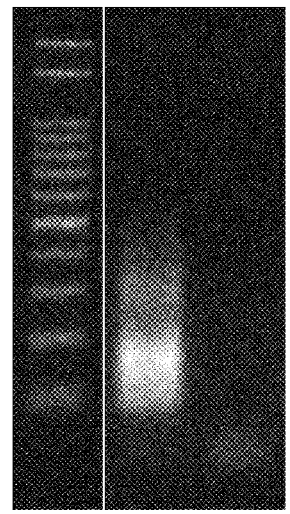
Figure 22:
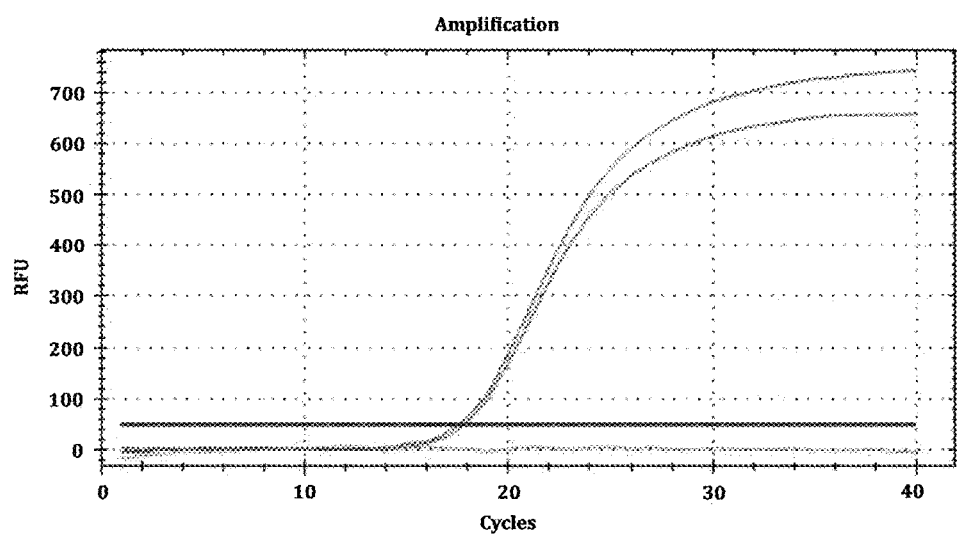
Figure 22:
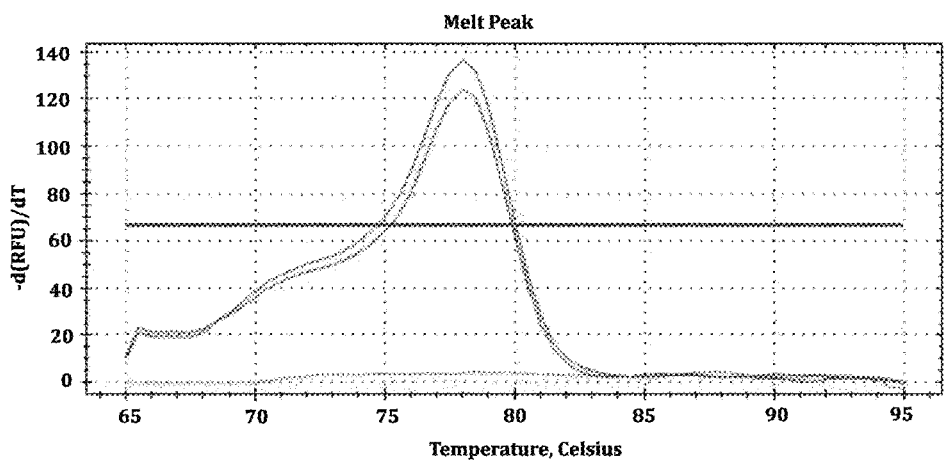
Figure 22:
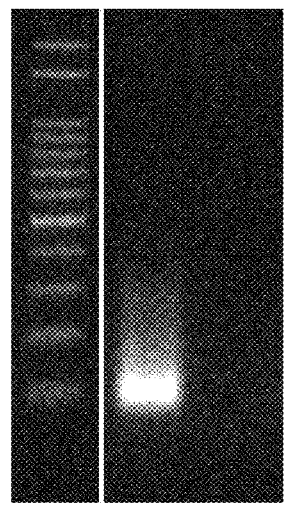
Figure 23:
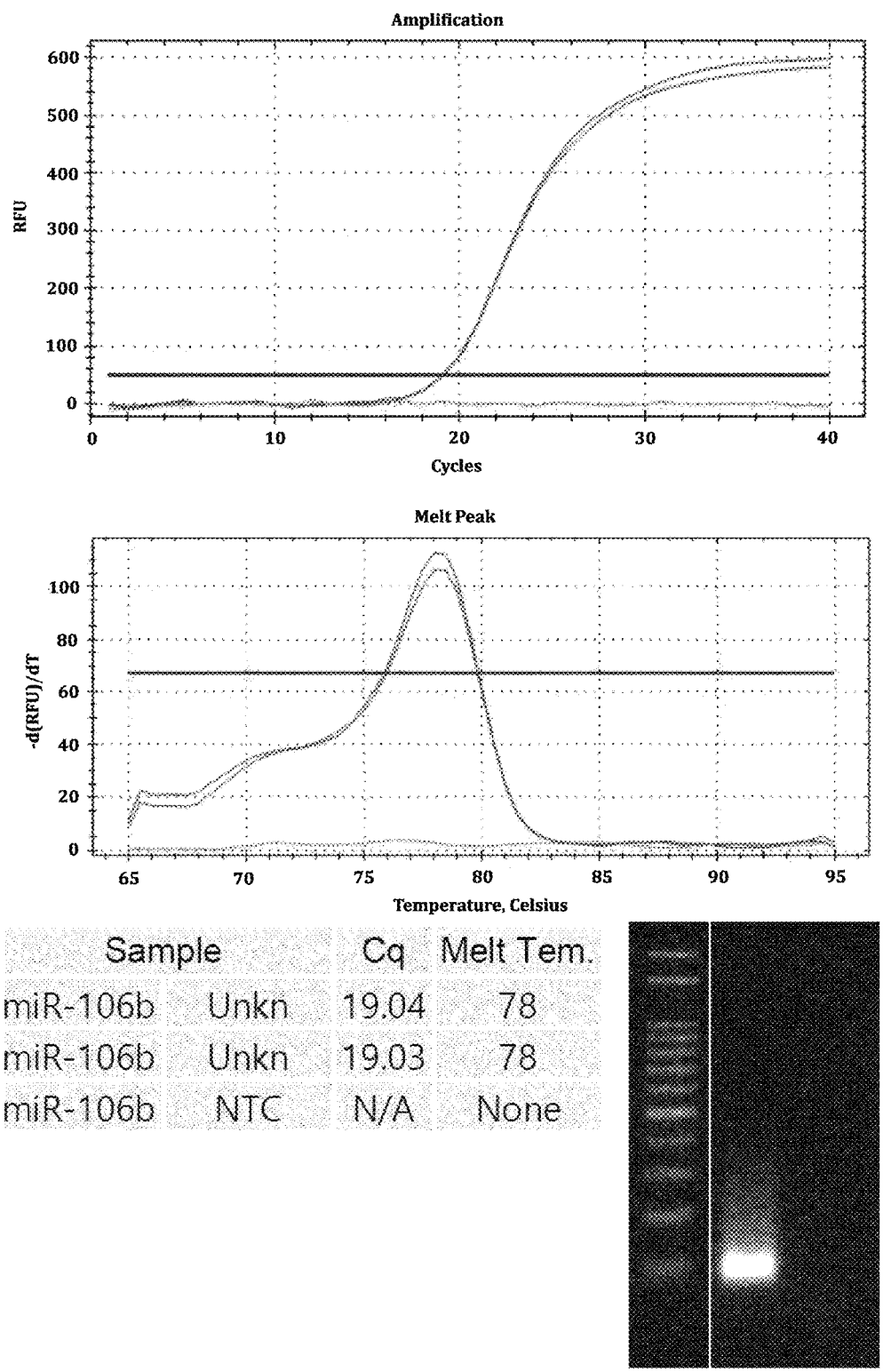
Figure 24:
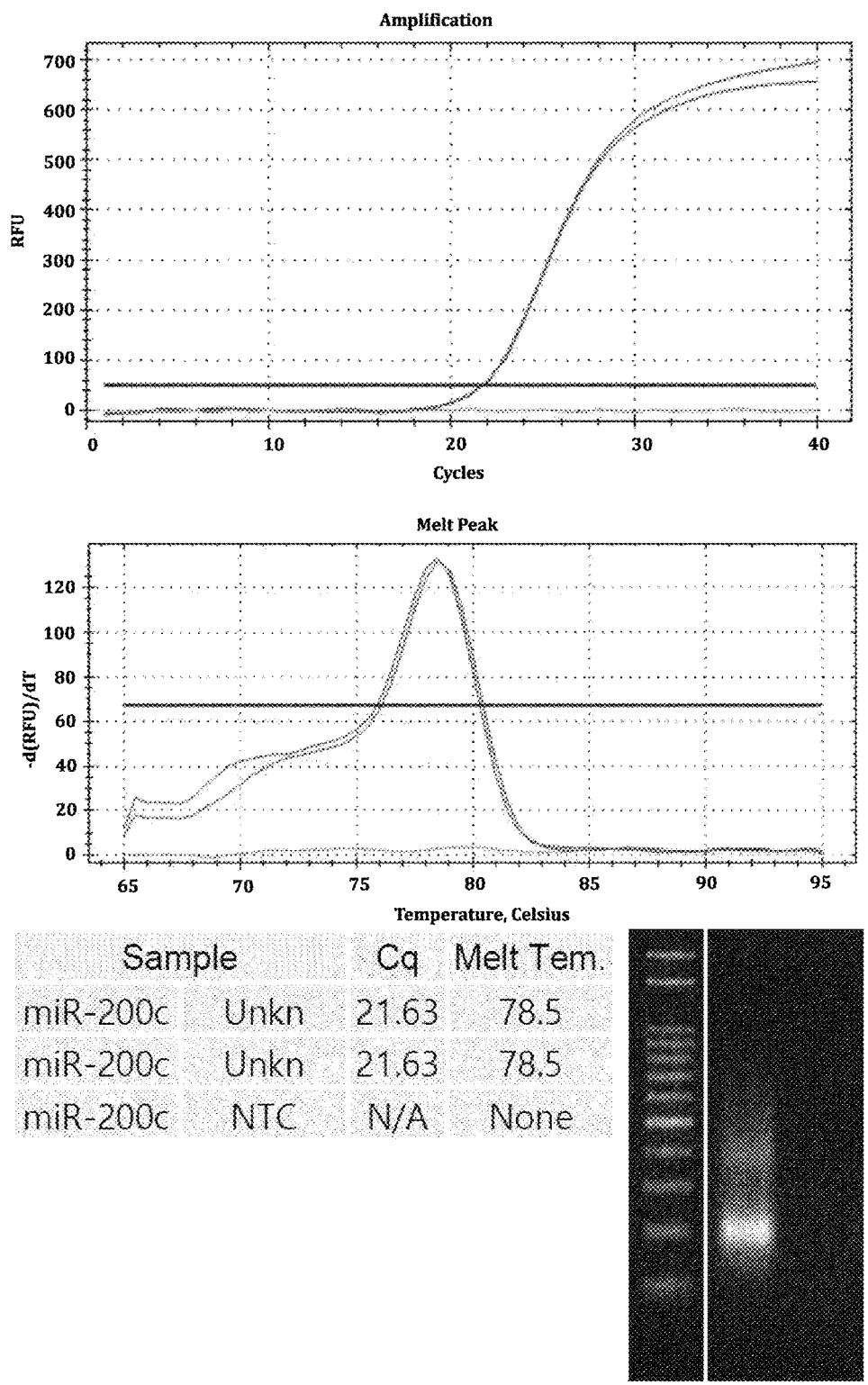
Figure 25:
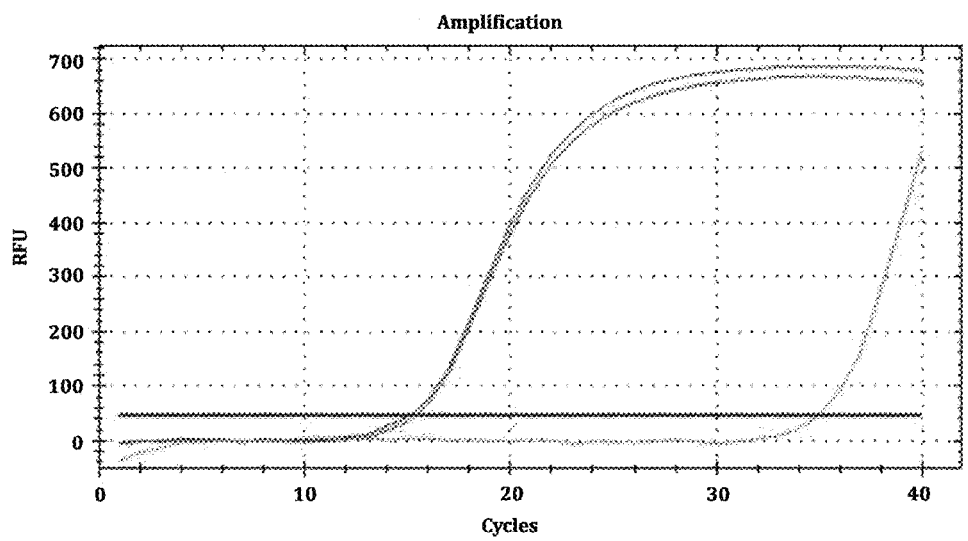
Figure 25:
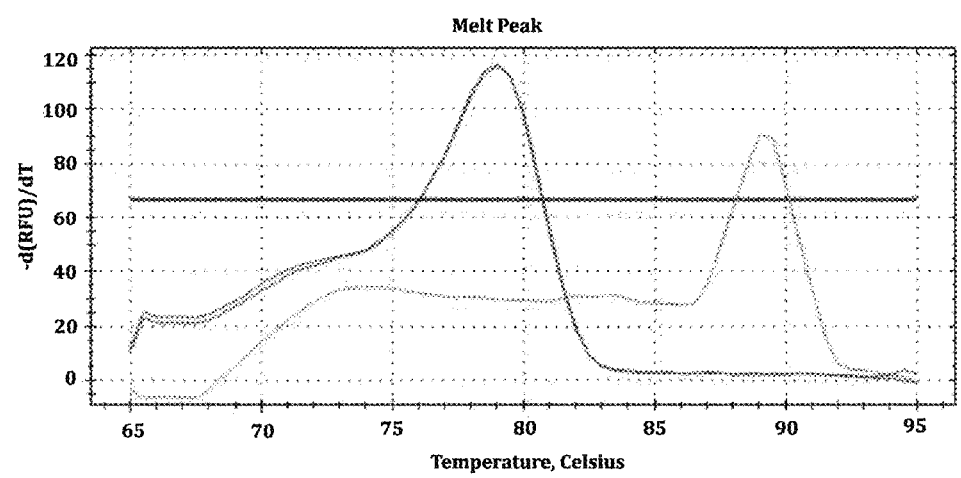
Figure 25:
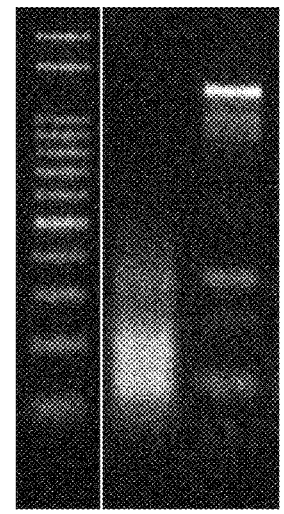
Figure 26:
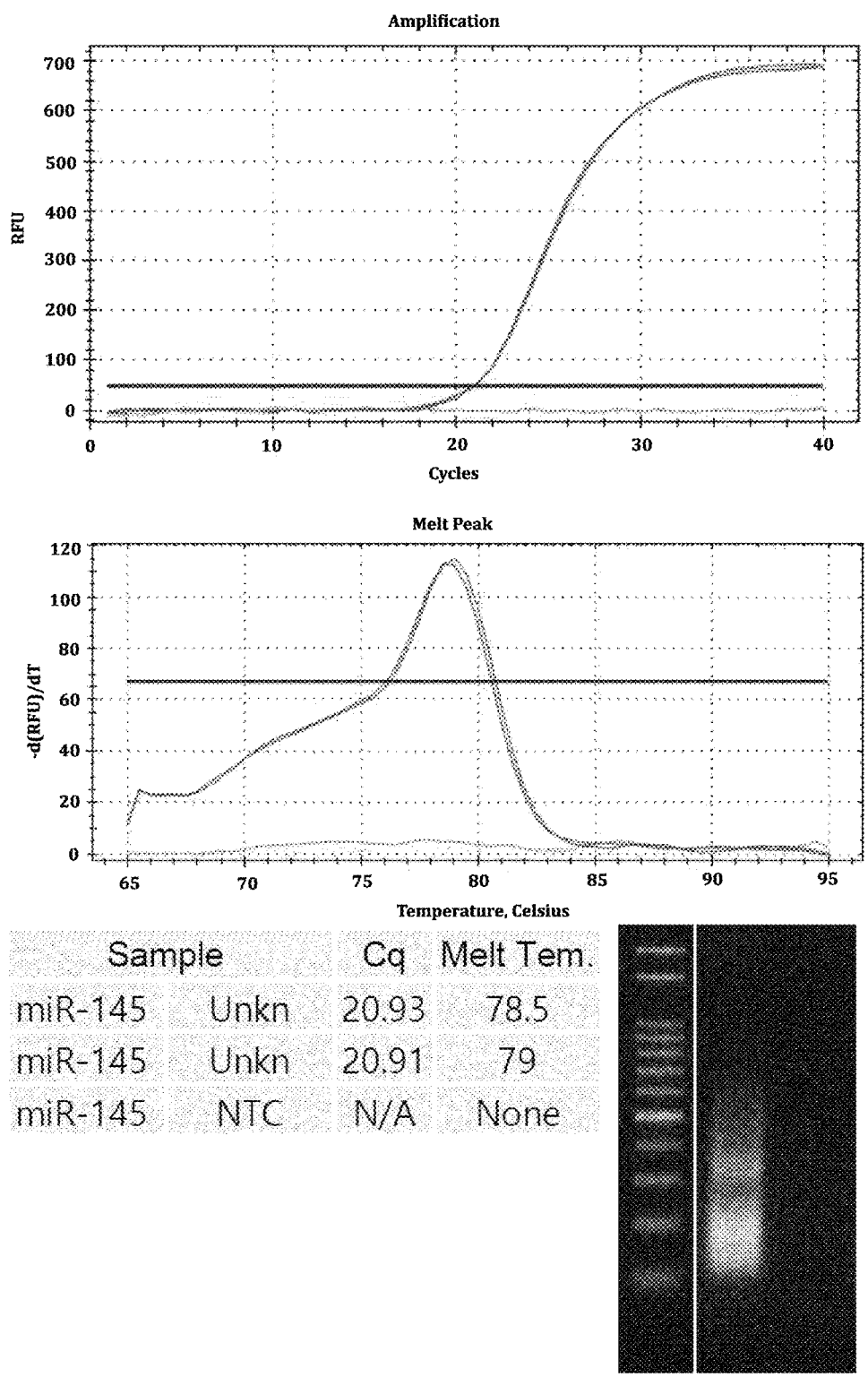

FIG. 2 is a schematic view illustrating a method of detecting miRNA using a miRNA-specific primer (reverse transcription primer) according to one embodiment of the present invention. As shown in FIG. 2, a miRNA-specific reverse primer 136 (short reverse transcription primer), consisting of a first hybridizing oligonucleotide 134 capable of binding complementarily to the 3-end' of a miRNA 101, and a first adaptor oligonucleotide 135 linked to the first hybridizing oligonucleotide and having any nucleic acid sequence that does not hybridize to a target miRNA, is hybridized to a 5-7-nt (preferably 6 nt) region of the 3'-end of the miRNA 101. Then, the miRNA 101 is subjected to reverse transcription using a reverse transcriptase, thereby producing an antisense strand cDNA 137. Then, the reverse transcriptase is deactivated, ensuring that the reverse transcription process is terminated, thereby preparing a single-stranded cDNA. When the antisense strand cDNA 137 is subjected to primer extension using an extension primer 143 (longer than the reverse transcription primer) composed of a second hybridizing oligonucleotide 138 capable of binding complementarily to a region (i.e., about 16 nt region) corresponding to the miRNA region excluding the above-described 6 nt region, and a second adaptor oligonucleotide 142 which is linked to the second hybridizing oligonucleotide 138 and which does not bind complementarily to both of the antisense strand cDNA 137 and the miRNA 101, the cDNA is then extended in both directions, thereby producing an extension product comprising strands complementary to the miRNA-specific primer 136 and to the second adaptor oligonucleotide 142.

Here, the second adaptor oligonucleotide 142 comprises a 5'-region 141 that is an universal primer region, which is used commonly in all miRNA detection kits, at its 5'-end and the remaining 3'-region 139 of the second adaptor oligonucleotide 142 may have different sequences and/or lengths depending on the kind of miRNA, so that various miRNAs may be detected at the same time by multiplex analysis. After completion of the primer extension, a PCR product 145 is produced by PCR using the miRNA-specific primer 136 and a forward primer 144 corresponding to the 5'-region 141. The forward primer 144 has a sequence within the nucleic acid sequence of the 5'-end of the second adaptor oligonucleotide. If the sequence of the 5'-end of the second adaptor oligonucleotide is designed to be constant regardless of the kind of miRNA, the forward primer 144 becomes a universal primer. The PCR product 145 can be detected by real-time PCR during the PCR reaction, and can be visualized by agarose gel electrophoresis or the like. The miRNA-specific primer can be used as a reverse primer for the PCR reaction. Alternatively, the reverse primer may be composed of at least part of the first adaptor oligonucleotide. In this case, the first adaptor oligonucleotide may have a constant sequence regardless of the kind of miRNA, and the reverse primer may be a universal primer.

According to the embodiments of the present invention, it is possible to detect a certain miRNA in a quick and accurate manner, and it also possible to perform multiplex analysis capable of detecting a plurality of miRNAs at the same time. Thus, the miRNA detection kit and method according to the embodiments of the present invention can be very effectively used to diagnose various diseases, including cancer, and determine prognosis of such diseases.

Of course, the scope of the present is not limited by the aforementioned effects.

Examples

Hereinafter, the present invention will be described with reference to non-limiting examples. It is to be understood, however, that these examples are for illustrative purposes only and are not intended to limit the scope of the present invention. Thus, those that can be easily contemplated by persons skilled in the art from the detailed description and examples of the present invention are interpreted to fall within the scope of the present invention.

In examples of the present invention, miRNA was tailed with poly(A), and then subjected to reverse transcription using oligo dT primers. Next, primer extension in both directions was performed using an extension primer comprising a miRNA-specific primer, and then various miRNAs were detected by PCR. In addition, in the examples of the present invention, various miRNAs were detected using a miRNA-specific primer (short reverse transcription primer) having a 6-nt nucleic acid sequence specific for the 3'-end of miRNA, and an extension primer (longer than the reverse transcription primer) having a miRNA-specific sequence excluding the 6-nt nucleic acid sequence, without using oligo dT primers. The miRNAs detected are shown in Table 1 below.

In the detection method performed using a poly(A) polymerase, poly(A) tailing and reverse transcription were performed at 42° C. for 60 minutes, and then the reverse transcriptase was deactivated by heating at 70° C. for 10 minutes. Primer extension and PCR were performed by melting DNA at 95° C. for 15 minutes, and then performing 40 cycles, each consisting of 94° C. for 15 sec, 55° C. for 30 sec, and 70° C. for 30 sec. Next, a melting curve was measured by heating at 95° C. for 10 sec, and then heating from 65° C. to 95° C. at a rate of 0.5° C. per 5 sec.

In the detection method performed using the miRNA-specific primer, reverse transcription was performed at 42° C. for 60 minutes, and then the reverse transcriptase was deactivated by heating at 70° C. for 10 minutes. Primer extension and PCR were performed by melting DNA at 95° C. for 15 minutes, and then performing 40 cycles, each consisting of 95° C. for 10 sec and 60° C. for 40 sec. Next, a melting curve was measured by heating at 95° C. for 10 sec, and then heating from 65° C. to 95° C. at a rate of 0.5° C. per 5 sec.

The PCR reaction was performed using a real-time PCR system (ABI), and whether or not the PCR reaction would be actually achieved was analyzed using 1.5% agarose gel electrophoresis band patterns.

TABLE 1

Examples of the present invention

| Example | miRNA to be amplified | Use of poly(A) polymerase | Reverse primer (SEQ ID NO) | Extension primer (SEQ ID NO) | Forward primer | Reverse primer |
|---|---|---|---|---|---|---|
| 1 | miR-532 | Y | 1 | 10 | 18 | 19 |
| 2 | miR-196b | Y |  | 11 |  |  |
| 3 | miR-362 | Y |  | 12 |  |  |
| 4 | miR-29c | Y |  | 13 |  |  |
| 5 | miR-106b | Y |  | 14 |  |  |
| 6 | miR-200c | Y |  | 15 |  |  |
| 7 | miR-127 | Y |  | 16 |  |  |
| 8 | miR-145 | Y |  | 17 |  |  |
| 9 | miR-532 | N | 2 | 10 |  | 2 |
| 10 | miR-196b | N | 3 | 11 |  | 3 |
| 11 | miR-362 | N | 4 | 12 |  | 4 |
| 12 | miR-29c | N | 5 | 13 |  | 5 |
| 13 | miR-106b | N | 6 | 14 |  | 6 |
| 14 | miR-200c | N | 7 | 15 |  | 7 |
| 15 | miR-127 | N | 8 | 16 |  | 8 |
| 16 | miR-145 | N | 9 | 17 |  | 9 |

Comparative Examples

In comparative examples, miRNAs were amplified using a commercial miRNA detection kit (Qiagen) in order to compare the performance of the miRNA detection kit of the present invention with the commercial miRNA detection kit (Qiagen).

TABLE 2

Comparative Examples

| Comparative Example | miRNA to be amplified | Detection method |
| --- | --- | --- |
| 1 | miR-532 | Use of anchor oligo dT adaptor |
| 2 | miR-196b | Use of anchor oligo dT adaptor |
| 3 | miR-362 | Use of anchor oligo dT adaptor |
| 4 | miR-29c | Use of anchor oligo dT adaptor |
| 5 | miR-106b | Use of anchor oligo dT adaptor |
| 6 | miR-200c | Use of anchor oligo dT adaptor |
| 7 | miR-127 | Use of anchor oligo dT adaptor |
| 8 | miR-145 | Use of anchor oligo dT adaptor |

The analysis results are shown in FIGS. 3 to 26. As can be seen therein, the miRNA detection kit and method according to the embodiments of the present invention enabled miRNAs to be detected more clearly and accurately than the commercial miRNA detection kit (Qiagen). According to the miRNA detection kit and method of the present invention, the short reverse transcription primer is used, and thus the time required for reverse transcription can be reduced to increase the overall PCR rate, making it possible to quickly detect miRNAs. In addition, since the extension primer longer than the reverse transcription primer is used in the primer extension step, a template having a sufficient length for use in PCR reaction can be prepared.

As described above, according to the embodiments of the present invention, it is possible to detect a certain miRNA in a quick and accurate manner, and it also possible to perform multiplex analysis capable of detecting a plurality of miRNAs at the same time. Thus, the miRNA detection kit and method according to the embodiments of the present invention can be very effectively used to diagnose various diseases, including cancer, and determine prognosis of such diseases.

Although the present invention has been described with reference to the embodiments, those skilled in the art will appreciate that these embodiments are illustrative only and various modifications and other equivalent embodiments are possible. Thus, the true technical scope of the present invention should be defined by the technical spirit of the appended claims.

We claim:

1. A method for detecting miRNA, comprising:

reverse-transcribing a miRNA using a reverse transcriptase and a short reverse transcription primer, in which the short reverse transcription primer is composed of a first hybridizing oligonucleotide and a first adaptor oligonucleotide, the first hybridizing oligonucleotide having a nucleic acid sequence which hybridizes specifically to the 3'-end of the miRNA, and the first adaptor oligonucleotide being attached to the 5'-end of the first hybridizing oligonucleotide and having any nucleic acid sequence which does not hybridize to the miRNA;

deactivating the reverse transcriptase and melting a DNA produced by the reverse transcription, thereby preparing a single-stranded cDNA reverse-transcribed from the miRNA;

extending the single-stranded cDNA using a DNA polymerase and an extension primer longer than the short reverse transcription primer, in which the extension primer is composed of a second hybridizing oligonucleotide and a second adaptor oligonucleotide, the second hybridizing oligonucleotide being capable of hybridizing specifically to a portion of the single-stranded cDNA reverse-transcribed from the miRNA, the portion of the single-stranded cDNA excluding a portion corresponding to the 3'-end of the miRNA, the 3'-end of the miRNA being hybridized to the first hybridizing oligonucleotide, and the second adaptor oligonucleotide being attached to the 5'-end of the second hybridizing oligonucleotide and having any nucleic acid sequence which does not hybridize to the single-stranded cDNA; and performing PCR amplification using as a template a double-strand cDNA produced by the extending and using a reverse primer having the same nucleic acid sequence as that of the reverse transcription primer or the first adaptor oligonucleotide, and a forward primer having a sequence within the sequence of the second adaptor oligonucleotide, wherein the short reverse transcription primer is 18 to 20 nt in length, and wherein the second adaptor oligonucleotide is 56 to 63 nt in length.

2. The method of claim 1, wherein the first hybridizing oligonucleotide is 3 to 12 nt in length.

3. The method of claim 1, wherein the PCR amplification is performed by real-time PCR reaction.

\* \* \* \* \*

SEQUENCE LISTING

```
<160> NUMBER OF SEQ ID NOS: 21

<210> SEQ ID NO 1
<211> LENGTH: 29
<212> TYPE: DNA
<213> ORGANISM: Artificial Sequence
<220> FEATURE:
<223> OTHER INFORMATION: primer for reversetranscription with poly A
      tailing

<400> SEQUENCE: 1
gcaccaccac tgattagttt tttttttt                                            29

<210> SEQ ID NO 2
<211> LENGTH: 18
<212> TYPE: DNA
<213> ORGANISM: Artificial Sequence
<220> FEATURE:
<223> OTHER INFORMATION: primer for the reversetranscription and reverse
      primer for PCR of hsa-miR-532

<400> SEQUENCE: 2
gcgagcatgc agacggtc                                                       18

<210> SEQ ID NO 3
<211> LENGTH: 20
<212> TYPE: DNA
<213> ORGANISM: Artificial Sequence
<220> FEATURE:
<223> OTHER INFORMATION: primer for the reversetranscription and reverse
      primer for PCR of hsa-miR-196b

<400> SEQUENCE: 3
gctagtcatg ccagcccaac                                                     20

<210> SEQ ID NO 4
<211> LENGTH: 19
<212> TYPE: DNA
<213> ORGANISM: Artificial Sequence
```

<220> FEATURE:
<223> OTHER INFORMATION: primer for the reversetranscription and reverse
      primer for PCR of hsa-miR-362

<400> SEQUENCE: 4
gcgagcatcg cagactcac                                                    19

<210> SEQ ID NO 5
<211> LENGTH: 19
<212> TYPE: DNA
<213> ORGANISM: Artificial Sequence
<220> FEATURE:
<223> OTHER INFORMATION: primer for the reversetranscription and reverse
      primer for PCR of hsa-miR-29c

<400> SEQUENCE: 5
gcgagcatcg cagtaaccg                                                    19

<210> SEQ ID NO 6
<211> LENGTH: 19
<212> TYPE: DNA
<213> ORGANISM: Artificial Sequence
<220> FEATURE:
<223> OTHER INFORMATION: primer for the reversetranscription and reverse
      primer for PCR of hsa-miR-106b

<400> SEQUENCE: 6
gcgagcactg cacatctgc                                                    19

<210> SEQ ID NO 7
<211> LENGTH: 20
<212> TYPE: DNA
<213> ORGANISM: Artificial Sequence
<220> FEATURE:
<223> OTHER INFORMATION: primer for the reversetranscription and reverse
      primer for PCR of hsa-miR-200c

<400> SEQUENCE: 7
gcgagcactt cacgtccatc                                                   20

<210> SEQ ID NO 8
<211> LENGTH: 18
<212> TYPE: DNA
<213> ORGANISM: Artificial Sequence
<220> FEATURE:
<223> OTHER INFORMATION: primer for the reversetranscription and reverse
      primer for PCR of hsa-miR-127

<400> SEQUENCE: 8
gcgacgatgc agagccaa                                                     18

<210> SEQ ID NO 9
<211> LENGTH: 20
<212> TYPE: DNA
<213> ORGANISM: Artificial Sequence
<220> FEATURE:
<223> OTHER INFORMATION: primer for the reversetranscription and reverse
      primer for PCR of hsa-miR-145

<400> SEQUENCE: 9
gcgagtccgc atagagggat                                                   20

<210> SEQ ID NO 10
<211> LENGTH: 77
<212> TYPE: DNA
<213> ORGANISM: Artificial Sequence
<220> FEATURE:

<223> OTHER INFORMATION: extension primer for hsa-miR-532

<400> SEQUENCE: 10

```
gcacctccag gaccaatctt gtagccagga tcttgccatc ctatggaact gcctcggtga    60
gcatgccttg agtgtag                                                   77
```

<210> SEQ ID NO 11
<211> LENGTH: 77
<212> TYPE: DNA
<213> ORGANISM: Artificial Sequence
<220> FEATURE:
<223> OTHER INFORMATION: extension primer for hsa-miR-196b

<400> SEQUENCE: 11

```
gcacctccag gaccaatctt gtagccagga tcttgccatc ctatggaact gcctcggtga    60
gtaggtagtt tcctgtt                                                   77
```

<210> SEQ ID NO 12
<211> LENGTH: 79
<212> TYPE: DNA
<213> ORGANISM: Artificial Sequence
<220> FEATURE:
<223> OTHER INFORMATION: extension primer for hsa-miR-362

<400> SEQUENCE: 12

```
gcacctccag gaccaatctt gtagccagga tcttgccatc ctatggaact gcctcggtga    60
gaatccttgg aacctaggt                                                 79
```

<210> SEQ ID NO 13
<211> LENGTH: 77
<212> TYPE: DNA
<213> ORGANISM: Artificial Sequence
<220> FEATURE:
<223> OTHER INFORMATION: extension primer for hsa-miR-29c

<400> SEQUENCE: 13

```
gcacctccag gaccaatctt gtagccagga tcttgccatc ctatggaact gcctcggtga    60
gtagcaccat ttgaaat                                                   77
```

<210> SEQ ID NO 14
<211> LENGTH: 76
<212> TYPE: DNA
<213> ORGANISM: Artificial Sequence
<220> FEATURE:
<223> OTHER INFORMATION: extension primer for hsa-miR-106b

<400> SEQUENCE: 14

```
gcacctccag gaccaatctt gtagccagga tcttgccatc ctatggaact gcctcggtga    60
gtaaagtgct gacagt                                                    76
```

<210> SEQ ID NO 15
<211> LENGTH: 78
<212> TYPE: DNA
<213> ORGANISM: Artificial Sequence
<220> FEATURE:
<223> OTHER INFORMATION: extension primer for hsa-miR-200c

<400> SEQUENCE: 15

```
gcacctccag gaccaatctt gtagccagga tcttgccatc ctatggaact gcctcggtga    60
gtaatactgc cgggtaat                                                  78
```

-continued

```
<210> SEQ ID NO 16
<211> LENGTH: 77
<212> TYPE: DNA
<213> ORGANISM: Artificial Sequence
<220> FEATURE:
<223> OTHER INFORMATION: extension primer for hsa-miR-127

<400> SEQUENCE: 16
gcacctccag gaccaatctt gtagccagga tcttgccatc ctatggaact gcctcggtga      60
gtcggatccg tctgagc                                                    77

<210> SEQ ID NO 17
<211> LENGTH: 78
<212> TYPE: DNA
<213> ORGANISM: Artificial Sequence
<220> FEATURE:
<223> OTHER INFORMATION: extension primer for hsa-miR-145

<400> SEQUENCE: 17
gcacctccag gaccaatctt gtagccagga tcttgccatc ctatggaact gcctcggtga      60
ggtccagttt tcccagga                                                   78

<210> SEQ ID NO 18
<211> LENGTH: 18
<212> TYPE: DNA
<213> ORGANISM: Artificial Sequence
<220> FEATURE:
<223> OTHER INFORMATION: universal forward primer for poly A tailed
      miRNA

<400> SEQUENCE: 18
gcacctccag gaccaatc                                                   18

<210> SEQ ID NO 19
<211> LENGTH: 17
<212> TYPE: DNA
<213> ORGANISM: Artificial Sequence
<220> FEATURE:
<223> OTHER INFORMATION: universal reverse primer for poly A tailed
      miRNA

<400> SEQUENCE: 19
gcaccaccac tgattag                                                    17

<210> SEQ ID NO 20
<211> LENGTH: 12
<212> TYPE: DNA
<213> ORGANISM: Artificial Sequence
<220> FEATURE:
<223> OTHER INFORMATION: poly(A) tail

<400> SEQUENCE: 20
aaaaaaaaaa aa                                                         12

<210> SEQ ID NO 21
<211> LENGTH: 12
<212> TYPE: DNA
<213> ORGANISM: Artificial Sequence
<220> FEATURE:
<223> OTHER INFORMATION: poly dT

<400> SEQUENCE: 21
tttttttttt tt                                                         12
```